US012797061B2

(12) United States Patent
Zeevi et al.

(10) Patent No.: US 12,797,061 B2
(45) Date of Patent: Nov. 17, 2026

(54) NON-SWIVEL SUTURE ANCHOR FOR KNOTLESS FIXATION OF TISSUE

(71) Applicant: OSSIO LTD., Caesarea (IL)

(72) Inventors: Tal Zeevi, Pardes Hana-Karkur (IL); Ido Ashpiz, Rosh Haayin (IL); Orahn Preiss-Bloom, Zichron Yaakov (IL)

(73) Assignee: OSSIO LTD, Caesarea (IL)

( * ) Notice: Subject to any disclaimer, the term of this patent is extended or adjusted under 35 U.S.C. 154(b) by 15 days.

(21) Appl. No.: 18/712,250

(22) PCT Filed: Nov. 24, 2022

(86) PCT No.: PCT/IL2022/051252
§ 371 (c)(1),
(2) Date: May 30, 2024

(87) PCT Pub. No.: WO2023/100173
PCT Pub. Date: Jun. 8, 2023

(65) Prior Publication Data

US 2024/0407777 A1 Dec. 12, 2024

Related U.S. Application Data

(60) Provisional application No. 63/284,213, filed on Nov. 30, 2021.

(51) Int. Cl.
*A61B 17/04* (2006.01)
*A61B 17/00* (2006.01)

(52) U.S. Cl.
CPC .................... *A61B 17/0401* (2013.01); *A61B 2017/00477* (2013.01); *A61B 2017/00964* (2013.01);
(Continued)

(58) Field of Classification Search
CPC .......... A61B 17/0401; A61B 2017/042; A61B 2017/0422; A61B 2017/0421; A61B 2017/0425; A61B 2017/0427; A61B 2017/0429; A61B 2017/043; A61B 2017/0432; A61B 2017/0433;
(Continued)

(56) References Cited

U.S. PATENT DOCUMENTS 4,655,777 A 4/1987 Dunn
4,750,905 A 6/1988 Koeneman
(Continued)

FOREIGN PATENT DOCUMENTS

CN 1168105 A 12/1997
CN 1214939 A 4/1999
(Continued)

OTHER PUBLICATIONS

Israel Office Action issued in IL Patent Application No. 294542 dated Feb. 1, 2025, 4 pages.
(Continued)

*Primary Examiner* — Shaun L David
*Assistant Examiner* — Cherie M Poland
(74) *Attorney, Agent, or Firm* — GRAESER ASSOCIATES INTERNATIONAL INC; Dvorah Graesesr

(57) ABSTRACT

A non-swivel suture anchor system to secure soft tissue to bone comprising a tip component which comprises a widened end portion and a shaft, and a cannulated screw.

15 Claims, 8 Drawing Sheets

(52) U.S. Cl.
CPC ................. *A61B 2017/0403* (2013.01); *A61B 2017/0409* (2013.01); *A61B 2017/0414* (2013.01); *A61B 2017/044* (2013.01)

(58) Field of Classification Search
CPC .................. A61F 2/0805; A61F 2/0811; A61F 2002/0858; A61F 2002/0835; A61F 2002/0888
See application file for complete search history.

(56) References Cited

U.S. PATENT DOCUMENTS

| | | | |
|---|---|---|---|
| 4,911,718 | A | 3/1990 | Lee |
| 5,064,439 | A | 11/1991 | Chang |
| 5,181,930 | A | 1/1993 | Dumbleton |
| 5,192,330 | A | 3/1993 | Chang |
| 5,312,669 | A | 5/1994 | Bedard |
| 5,338,772 | A | 8/1994 | Bauer |
| 5,522,817 | A | 6/1996 | Sander |
| 5,522,904 | A | 6/1996 | Moran |
| 5,674,294 | A | 10/1997 | Bainville |
| 5,679,299 | A | 10/1997 | Gilbert |
| 6,004,650 | A | 12/1999 | Schweizer |
| 6,171,338 | B1 | 1/2001 | Talja |
| 6,299,649 | B1 | 10/2001 | Chang |
| 6,306,140 | B1 | 10/2001 | Siddiqui |
| 6,352,667 | B1 | 3/2002 | English |
| 6,471,707 | B1 | 10/2002 | Miller |
| 6,511,511 | B1 | 1/2003 | Slivka |
| 6,602,293 | B1 | 8/2003 | Biermann |
| 6,916,321 | B2 | 7/2005 | Tenhuisen |
| 7,541,049 | B1 | 6/2009 | Toermaelae |
| 7,918,879 | B2 | 4/2011 | Yeung |
| 7,947,069 | B2 | 5/2011 | Sanders |
| 8,702,716 | B1 | 4/2014 | Stein |
| 8,709,055 | B2 | 4/2014 | Beyar |
| 8,735,504 | B2 | 5/2014 | Clay |
| 8,992,622 | B2 | 3/2015 | Ullrich, Jr. |
| 9,186,302 | B2 | 11/2015 | Kilway |
| 9,456,890 | B2 | 10/2016 | Day |
| 9,649,104 | B2 | 5/2017 | Lunn |
| 9,788,832 | B2 | 10/2017 | Hadba |
| 10,926,004 | B2 | 2/2021 | Preiss-Bloom |
| 11,020,110 | B1 | 6/2021 | Blair |
| 12,239,766 | B2 | 3/2025 | Orahn |
| 2002/0115999 | A1* | 8/2002 | McDevitt ........... A61B 17/0401 606/60 |
| 2003/0204195 | A1 | 10/2003 | Keane |
| 2005/0118326 | A1 | 6/2005 | Anfinsen |
| 2005/0177245 | A1 | 8/2005 | Leatherbury |
| 2005/0216016 | A1 | 9/2005 | Contiliano |
| 2005/0226904 | A1 | 10/2005 | Choi |
| 2005/0228500 | A1 | 10/2005 | Kim |
| 2005/0240199 | A1 | 10/2005 | Martinek |
| 2006/0020266 | A1 | 1/2006 | Cooper |
| 2006/0021270 | A1 | 2/2006 | Hanley |
| 2006/0095134 | A1 | 5/2006 | Trieu |
| 2006/0154206 | A1 | 7/2006 | Petersson |
| 2006/0178748 | A1 | 8/2006 | Dinger, III |
| 2006/0235413 | A1 | 10/2006 | Denham |
| 2006/0271060 | A1 | 11/2006 | Gordon |
| 2007/0150059 | A1 | 6/2007 | Ruberte |
| 2007/0185568 | A1 | 8/2007 | Schwartz |
| 2007/0219557 | A1 | 9/2007 | Bourque |
| 2007/0270969 | A1 | 11/2007 | Schmid |
| 2007/0282455 | A1 | 12/2007 | Luginbuehl |
| 2008/0051836 | A1 | 2/2008 | Foerster |
| 2008/0208253 | A1 | 8/2008 | Dreyfuss |
| 2008/0215091 | A1 | 9/2008 | Dreyfuss |
| 2008/0255561 | A1 | 10/2008 | Tormala |
| 2009/0112317 | A1 | 4/2009 | Li |
| 2009/0216233 | A1 | 8/2009 | Wiedrich |
| 2009/0234387 | A1 | 9/2009 | Miller |
| 2009/0240337 | A1 | 9/2009 | Myung |
| 2009/0258965 | A1 | 10/2009 | Lassila |
| 2009/0304761 | A1 | 12/2009 | Rabiei |
| 2009/0312794 | A1 | 12/2009 | Nason |
| 2010/0119564 | A1 | 5/2010 | Kasuga |
| 2010/0121463 | A1 | 5/2010 | Toermaelae |
| 2010/0168798 | A1 | 7/2010 | Clineff |
| 2010/0179573 | A1 | 7/2010 | Levinsohn |
| 2010/0292732 | A1* | 11/2010 | Hirotsuka ............... B29C 45/00 606/232 |
| 2011/0098826 | A1 | 4/2011 | Mauck |
| 2011/0166659 | A1 | 7/2011 | Luginbuehl |
| 2011/0282395 | A1 | 11/2011 | Beyar |
| 2012/0016373 | A1 | 1/2012 | Impellizzeri |
| 2012/0040002 | A1 | 2/2012 | Lehtonen |
| 2012/0040015 | A1 | 2/2012 | Lehtonen |
| 2012/0040137 | A1 | 2/2012 | Palasis |
| 2012/0191214 | A1 | 7/2012 | Nies |
| 2012/0265206 | A1 | 10/2012 | Jang |
| 2013/0144400 | A1 | 6/2013 | Day |
| 2013/0204368 | A1 | 8/2013 | Prevost |
| 2013/0218291 | A1 | 8/2013 | Giorno |
| 2013/0296500 | A1 | 11/2013 | Clay |
| 2013/0317555 | A1 | 11/2013 | Schaller |
| 2014/0018809 | A1 | 1/2014 | Allen |
| 2014/0114330 | A1 | 4/2014 | Karasic |
| 2014/0257381 | A1* | 9/2014 | Palese ................ A61B 17/0401 606/232 |
| 2014/0364862 | A1 | 12/2014 | Bennett |
| 2015/0238655 | A1 | 8/2015 | Jongpaiboonkit |
| 2015/0245901 | A1 | 9/2015 | Dougherty |
| 2015/0289979 | A1 | 10/2015 | Gabele |
| 2016/0011369 | A1 | 1/2016 | Doyle |
| 2016/0113695 | A1 | 4/2016 | Globerman |
| 2016/0135801 | A1 | 5/2016 | Lombardo |
| 2016/0172562 | A1 | 6/2016 | Voutsas |
| 2016/0278789 | A1 | 9/2016 | Garvey |
| 2016/0310129 | A1 | 10/2016 | Hoeppner |
| 2016/0374795 | A1 | 12/2016 | Dougherty |
| 2017/0172560 | A1* | 6/2017 | Patel .................. A61B 17/0401 |
| 2017/0172562 | A1 | 6/2017 | Lombardo |
| 2017/0181785 | A1 | 6/2017 | Beyar |
| 2017/0246356 | A1 | 8/2017 | Preiss-Bloom |
| 2018/0071080 | A1 | 3/2018 | Greelis |
| 2019/0167254 | A1 | 6/2019 | Balboa |
| 2019/0261974 | A1* | 8/2019 | Arai ................... A61B 17/0401 |
| 2020/0016846 | A1 | 1/2020 | Davidson |
| 2020/0155140 | A1 | 5/2020 | Palese |
| 2020/0245997 | A1* | 8/2020 | Balboa ............... A61B 17/0401 |
| 2021/0022725 | A1 | 1/2021 | Burkhart |
| 2021/0128137 | A1* | 5/2021 | Rogers ............... A61B 17/0401 |
| 2021/0161571 | A1 | 6/2021 | Haziza |
| 2021/0205505 | A1 | 7/2021 | Preiss-Bloom |
| 2021/0290217 | A1 | 9/2021 | Biedermann |
| 2021/0299332 | A1 | 9/2021 | Dias |
| 2021/0338225 | A1 | 11/2021 | Patel |
| 2021/0369314 | A1* | 12/2021 | Preiss-Bloom ....... A61L 31/128 |
| 2022/0008615 | A1 | 1/2022 | Cige |
| 2022/0054122 | A1 | 2/2022 | Bowman |
| 2022/0079576 | A1 | 3/2022 | Rogers |
| 2023/0024165 | A1 | 1/2023 | Preiss-Bloom |
| 2023/0380829 | A1 | 11/2023 | Zeevi |
| 2024/0124661 | A1 | 4/2024 | D'Agostino |

FOREIGN PATENT DOCUMENTS

| | | | |
|---|---|---|---|
| CN | 1371664 | A | 10/2002 |
| CN | 1565396 | A | 1/2005 |
| CN | 1593356 | A | 3/2005 |
| CN | 1668255 | A | 9/2005 |
| CN | 1953719 | A | 4/2007 |
| CN | 101106957 | A | 1/2008 |
| CN | 101420991 | A | 4/2009 |
| CN | 101437467 | A | 5/2009 |
| CN | 101790559 | B | 7/2010 |
| CN | 101942709 | A | 1/2011 |
| CN | 102281907 | A | 12/2011 |
| CN | 102395329 | A | 3/2012 |
| CN | 102421463 | A | 4/2012 |
| CN | 102421716 | A | 4/2012 |
| CN | 103747813 | A | 4/2014 |

(56) References Cited

FOREIGN PATENT DOCUMENTS

| | | | | |
|---|---|---|---|---|
| CN | 104188706 A | | 12/2014 | |
| CN | 106392332 A | | 2/2017 | |
| EP | 0373294 A2 | | 6/1990 | |
| EP | 1716874 A2 | | 11/2006 | |
| EP | 2243500 A1 | | 10/2010 | |
| EP | 2243749 A1 | | 10/2010 | |
| EP | 2292166 A1 | | 3/2011 | |
| EP | 17819487 | | 6/2017 | |
| EP | 3236866 | | 11/2017 | |
| EP | 3320877 A1 | | 5/2018 | |
| EP | 3678566 | | 7/2020 | |
| EP | 3689259 | | 8/2020 | |
| EP | 3689259 A1 | * | 8/2020 | A61B 17/0401 |
| EP | 3678566 B1 | * | 9/2024 | B29C 70/86 |
| JP | 6415040 | | 1/1989 | |
| JP | H02121652 | | 5/1990 | |
| JP | 2002501418 A | | 1/2002 | |
| JP | 2004160157 | | 6/2004 | |
| JP | 2008200510 | | 9/2008 | |
| JP | 2009541568 | | 11/2009 | |
| JP | 2010526200 | | 7/2010 | |
| JP | 2012524569 | | 10/2012 | |
| WO | 9609014 A1 | | 3/1996 | |
| WO | 1996009014 | | 3/1996 | |
| WO | 9819616 | | 5/1998 | |
| WO | 1998019617 A1 | | 5/1998 | |
| WO | 9853768 A1 | | 12/1998 | |
| WO | 0132072 | | 5/2001 | |
| WO | 2005077039 A2 | | 8/2005 | |
| WO | 2005077039 A3 | | 8/2005 | |
| WO | 2006114483 | | 11/2006 | |
| WO | 2008095046 A2 | | 8/2008 | |
| WO | 2010122019 A1 | | 10/2010 | |
| WO | 2010122098 A2 | | 10/2010 | |
| WO | 2013116624 A1 | | 8/2013 | |
| WO | 2013164631 | | 11/2013 | |
| WO | 2016035088 A1 | | 3/2016 | |
| WO | 2016035089 | | 3/2016 | |
| WO | 2016103049 A1 | | 6/2016 | |
| WO | 2017155956 A1 | | 9/2017 | |
| WO | 2018002917 | | 1/2018 | |
| WO | 2019049062 | | 3/2019 | |
| WO | WO-2019049062 A1 | * | 3/2019 | A61B 17/866 |
| WO | 2019123462 | | 6/2019 | |
| WO | 2020044327 | | 3/2020 | |
| WO | 2021247707 A1 | | 12/2021 | |
| WO | 2023002471 | | 1/2023 | |

OTHER PUBLICATIONS

Office Action (Non-Final Rejection) dated Apr. 18, 2025 for U.S. Appl. No. 18/193,265 (pp. 1-20).
Office Action (Notice of Allowance and Fees Due (PTOL-85)) dated Jan. 15, 2025 for U.S. Appl. No. 17/859,039 (pp. 1-8).
Feih, S., Wonsyld, K., Minzari, D., Westermann, P., & Lilholt, H. (2004). Testing Procedure for the Single Fiber Fragmentation Test. Risø National Laboratory. Denmark. Forskningscenter Risoe. Risoe-R No. 1483(EN) 31 pages.
Ferri JM et al., "The effect of beta-tricalcium phosphate on mechanical and thermal performances of poly(lactic acid)", J Composite Materials 2016; 0(0): 1-10.
Hyon et al., "Effects of Residual Monomer on the Degradation of DL-Lactide Polymer" Polymer International 46 (1998) 196-202.
Indian Examination Report for App. No. IN201827049363, dated Nov. 18, 2021, 5 pages.
Indian Examination Report issued in App. No. IN202027011276, dated Apr. 27, 2022, 7 pages.
International Search Report issued in PCT/IL2019/050843, dated Nov. 6, 2019, 3 pages.
IP Office of Singapore Written Opinion for Application No. SG11201610671P, dated Aug. 14, 2019, 5 pages.
ISR from PCT/IL2022/050711 dated Oct. 19, 2022, 5 pages.
ISR from PCT/IL2022/051252 dated Feb. 9, 2023, 5 pages.
Japanese Office Action (includig English translation) issued in App. No. JP2020-511984, dated Aug. 2, 2022, 13 pages.
Japanese Office Action (including English translation) for App. No. JP2018-567587, dated Jan. 5, 2022, 5 pages.
Japanese Office Action (with English language translation) for Application No. 2017-504425, dated May 28, 2019, 7 pages.
Japanese Office Action (with English language translation) for Application No. JP2017-504425, dated Jan. 7, 2020, 6 pages.
Japanese Office Action (with English language translation) for Application No. JP2017-527796, mailing date Nov. 5, 2019, 6 pages.
Juan David Vanegas-Jaramillo, Ivan David Patiño-Arcilaa, Fragmentation model for the tensile response of unidirectional composites based on the critical number of fiber breaks and the correction of the fiber-matrix interfacial strength Latin American Journal of Solids and Structures, 2019, 16(7), e217, 27 pages.
Jurij Štalc, Luke D. Cicchinelli, Stuart Miller, Carolyn M. Sofka, Martinus Richter Fiber-reinforced fixation implant for proximal interphalangeal joint arthrodesis shows advanced implant bio-integration at 2-year follow-up Foot Ankle Surg. Jun. 23, 2022:S1268-7731(22)00117-5, 7 pages.
Korean Office Action (including English translation) for App. No. KR10-2019-7001863, dated Jan. 20, 2022, 13 pages.
Korean Office Action issued in App. No. KR10-2017-7018042, dated Aug. 17, 2022, 7 pages.
Kulkova J. et al., "Hydroxyapatite and bioactive glass surfaces for fiber reinforced composite implants via surface ablation by Excimer laser", Journal of the Mechanical Behavior of Biomedical Materials, vol. 75, doi: 10.1016/j.jmbbm.2017.07.005, (20170000), pp. 89-96, (Jul. 4, 2017), XP055696388.
Li Sijiao, "Modern Chromatographic Analysis", p. 118, National Defense Industry Press, Jun. 2014 (3 pages).
Miwa, M., Horiba, N. Effects of fiber length on tensile strength of carbon/glass fiber hybrid composites. Journal of Materials Science 29, 973-977 (1994).
Miwa, M., Ohsawa, T., and Tahara, K. (1980), Effects of fiber length on the tensile strength of epoxy/glass fiber and polyester/glass fiber composites. J. Appl. Polym. Sci., 25: 795-807 (Abstract).
Notice of Allowance dated Aug. 20, 2020 for U.S. Appl. No. 15/509,301 (pp. 1-9).
Notice of Allowance dated Aug. 28, 2020 for U.S. Appl. No. 16/081,605 (pp. 1-14).
Notice of Allowance dated Oct. 22, 2020 for U.S. Appl. No. 15/523,389 (pp. 1-6).
Office Action (Final Rejection) dated Feb. 22, 2023 for U.S. Appl. No. 17/152,165 (pp. 1-15).
Office Action (Final Rejection) dated Oct. 28, 2022 for U.S. Appl. No. 16/951,109 (pp. 1-7).
Office Action (Non-Final Rejection) dated Jul. 21, 2022 for U.S. Appl. No. 16/951,109 (pp. 1-8).
Office Action (Non-Final Rejection) dated Nov. 7, 2022 for U.S. Appl. No. 17/152,165 (pp. 1-15).
Office Action (Non-Final Rejection) dated Nov. 25, 2022 for U.S. Appl. No. 16/770,091 (pp. 1-22).
Office Action (Notice of Allowance and Fees Due (PTOL-85)) dated Jan. 18, 2022 for U.S. Appl. No. 16/637,363 (pp. 1-9).
Office Action (Notice of Allowance and Fees Due (PTOL-85)) dated Feb. 8, 2022 for U.S. Appl. No. 16/311,784 (pp. 1-6).
Office Action (Notice of Allowance and Fees Due (PTOL-85)) dated Feb. 15, 2023 for U.S. Appl. No. 16/951,109 (pp. 1-8).
Office Action (Notice of Allowance and Fees Due (PTOL-85)) dated Feb. 22, 2022 for U.S. Appl. No. 16/311,784 (pp. 1-3).
Office Action (Notice of Allowance and Fees Due (PTOL-85)) dated Mar. 29, 2022 for U.S. Appl. No. 16/637,363 (pp. 1-6).
Office Action dated Apr. 7, 2021 for U.S. Appl. No. 16/311,784 (pp. 1-11).
Office Action dated Aug. 5, 2019 for U.S. Appl. No. 15/509,274 (pp. 1-19).
Office Action dated Dec. 26, 2019 for U.S. Appl. No. 15/509,274, 18 pages.
Office Action dated Feb. 10, 2020, for U.S. Appl. No. 16/081,605 (pp. 1-17).

(56) References Cited

OTHER PUBLICATIONS

Office Action dated Jan. 13, 2020 for U.S. Appl. No. 15/523,389 (pp. 1-11).
Office Action dated Jul. 13, 2020 for U.S. Appl. No. 15/523,389 (pp. 1-12).
Office Action dated Nov. 18, 2019 for U.S. Appl. No. 16/081,605 (pp. 1-19).
Office Action dated Nov. 19, 2020 for U.S. Appl. No. 16/311,784 (pp. 1-14).
Office Action dated Nov. 7, 2019 for U.S. Appl. No. 15/523,389 (pp. 1-11).
Office Action dated Sep. 23, 2021 for U.S. Appl. No. 16/311,784 (pp. 1-11).
P. Amuthakkannan, V. Manikandan, J.T. Winowlin Jappes, M. Uthayakumar Effect of Fibre Length and Fibre Content on Mechanical Properties of Short Basalt Fibre Reinforced Polymer Matrix Composites Materials Physics and Mechanics 16 (2013) 107-117.
Polymer-Matrix Composites: Structure and Processing Deborah D.L. Chung, in Carbon Composites (Second Edition), 2017 3.3.4 Fiber Fragmentation Testing, 13 pages.
Rodricks CW, Greenfeld I, Fiedler B, Wagner HD. Fragmentation of Beaded Fibres in a Composite. Materials (Basel). Jan. 24, 2022;15(3):890, 22 pages.
Scholz et al., "The use of composite materials in modern orthopaedic medicine and prosthetic devices: A review", Composites Science and Technology, Elsevier, Amsterdam, NL, www.elsevier.com/locate/compscitech, vol. 71, No. 16 (2011) pp. 1791-1803.
Search report for parent PCT application No. PCT/IL2015/050903, mailed on Jan. 7, 2016 (13 pages).
Shia, David & Hui, Chung Yuen & Phoenix, S .. (2000). Statistics of fragmentation in a single-fiber composite under matrix yielding and debonding with application to the strength of multi-fiber composites. Composites Science and Technology. 60. 2107-2128. 10.1016/S0266-3538(00)00115-9. (Abstract) 7 pages.
Shiqiang Deng, Lin Ye, Yiu-Wing Mai, Hong-Yuan Liu, Evaluation of fibre tensile strength and fibre/matrix adhesion using single fibre fragmentation tests, Composites Part A: Applied Science and Manufacturing, vol. 29, Issue 4, 1998, pp. 423-434 (Abstract).
Supplementary European Search Report for EP15837823 dated Mar. 28, 2018, 6 pgs.
Wang et al., "Promising Poly(E-caprolactone) composite reinforced with weft-knitted polyester for small-diameter vascular graft application", Advances in Materials Science and Engineering, 2014, vol. 2014, p. 273891, 11 pages.
Website downloaded Aug. 23, 2022 (https://www.orthobullets.com/basic-science/9062/material-properties) 11 pages.
Wegener et al., "Microstructure, cytotoxicity and corrosion of powder-metallurgical iron alloys for biodegradable bone ematerials", Materials Science & Engineering. B. Advanced Functional Solid-State Materials, 2011, vol. 176, No. 20, p. 1789-1796.
Wei Junjie, "Medical Organic Chemistry Learning Guide", p. 300, Heilongjiang Science and Technology Press, Jan. 19 (7 pages).
WOISA from PCT/IL2022/051252 dated Feb. 9, 2023, 8 pages.
WOSA from PCT/IL2022/050711 dated Oct. 19, 2022, 6 pages.
Office Action (Final Rejection) dated Sep. 11, 2025 for U.S. Appl. No. 18/193,265 (pp. 1-30).
Written Opinion dated Dec. 21, 2023 for parent PCT application PCT/IL2023/051093 (pp. 1-9).
Arthrex Inc., "BioComposite Interference Screws—A Stronger turn in ACL/PCL Reconstruction", Scientific Research and Development, (20100000), URL: http://www.arthrex.com/knee/biocomposite-interference-screws. (6 pages).
Australian Examination Report No. 1 for App. No. AU2017287968, dated Aug. 31, 2021, 3 pages.
Australian Examination Report No. 1 for App. No. AU2017287968, dated Feb. 12, 2021, 4 pages.
Australian Examination Report No. 1 for Application No. 2015310510, dated Aug. 10, 2019, 6 pages.
Australian Examination Report No. 1 for Application No. AU2015370600, dated Oct. 2, 2019, 3 pages.
Australian Examination Report No. 2 for Application No. AU2015310510, dated Dec. 1, 2019, 3 pages.
Australian Examination Report No. 2 for Application No. AU2015370600, dated Jan. 29, 2020, 2 pages.
Brazilian Search Report (with English language translation) for App No. BR112017001049-6, dated Apr. 8, 2020, 8 pages.
Brazilian Technical Report (with English language translation) for App No. BR112017012508-0, dated Apr. 8, 2020, 7 pages.
C. Capelaa, S. E. Oliveiraa, J. Pestanaa, J.A.M. Ferreira, "Effect of fiber length on the mechanical properties of high dosage carbon reinforced", Procedia Structural Integrity 5 (2017) 539-546.
Canadian Office Action for App. No. CA2,955,392, dated Sep. 27, 2021, 15 pages.
Canadian Office Action issued in App. No. CA2,955,392, dated May 31, 2022, 4 pages.
Chinese Office Action (including English translation) for App. No. CN201780025291.1, dated Aug. 10, 2021, 12 pages.
Chinese Office Action (including English translation) for App. No. CN201780025291.1, dated Jan. 28, 2021, 12 pages.
Chinese Office Action (including English translation) for App. No. CN201980053932.3, dated Jan. 13, 2022, 10 pages.
Chinese Office Action (including English translation) issued in App. No. CN201880057783.3, dated Aug. 2, 2022, 16 pages.
Chinese Office Action (with English language translation) for App No. CN201580070362.0, datetd May 20, 2020, 9 pages.
Chinese Office Action (with English language translation) for Application No. 201580036606.3, dated Mar. 12, 2019, 13 pages.
Chinese Office Action (with English language translation) for Application No. CN201580036606.3, dated Oct. 25, 2019, 9 pages.
Chinese Office Action (with English language translation) for Application No. CN201580037255.8, dated Aug. 26, 2019, 16 pages.
Chinese Office Action (with English language translation) for Application No. CN201580070362.0, dated Aug. 29, 2019, 10 pages.
Chinese Office Action (with English translation) for App. No. CN201780053086.6, dated May 7, 2022, 21 pages.
Chinese Office Action (with English translation) for App. No. CN201780053086.6, dated Oct. 19, 2021, 15 pages.
Chinese Office Action dated Jul. 13, 2018 for corresponding CN Patent Application No. 201580037255.8, 9 pages.
Chinese Office Action for App. No. CN201780053086.6, dated Feb. 18, 2021, 23 pages.
Chinese Office Action for App. No. CN201880057783.3, dated Dec. 2, 2021, 15 pages.
Chinese Office Action for Appl. No. 201580037255.8, dated Mar. 26, 2019, 7 pages.
Chinese Third Office Action (with English translation) for App. No. CN201780053086.6, dated Feb. 16, 2022, 13 pages.
Composites Encyclopedia, WO Dingzhu et al., pp. 519-520, Beijing: Chemical Industry Press, Jan. 2001, (pp. 7-12).
Corrected Notice of Allowability dated Dec. 23, 2020 for U.S. Appl. No. 15/523,389 (pp. 1-3).
Corrected Notice of Allowability dated Oct. 19, 2020 for U.S. Appl. No. 16/081,605 (pp. 1-9).
Corrected Notice of Allowability dated Oct. 7, 2020 for U.S. Appl. No. 15/509,301 (pp. 1-6).
English translation of Chinese Office Action issued in App. No. CN201780025291.1, dated Apr. 9, 2022, 6 pages.
English translation of Chinese Office Action issued in App. No. CN201880057783.3, dated Dec. 2, 2021, 11 pages.
English translation of Japanese Office Action for App. No. JP2018-567587, dated Mar. 23, 2021, 4 pages.
English translation of Japanese Office Action issued in App. No. JP2018-567587, dated Jul. 5, 2022, 4 pages.
English translation of Japanese Office Action issued in App. No. JP2020-534895, dated Oct. 4, 2022, 3 pages.
European Patent Office Communication pursuant to Article 94(3) EPC for App. No. EP17763876.4, dated Aug. 19, 2020, 9 pages.
European Patent Office Communication pursuant to Article 94(3) EPC for App. No. EP17763876.4, dated Jan. 4, 2022, 8 pages.
European Patent Office Communication pursuant to Article 94(3) EPC for App. No. EP17819487.4, dated Jun. 21, 2021, 5 pages.

(56) References Cited

OTHER PUBLICATIONS

European Patent Office Communication pursuant to Article 94(3) EPC issued in App. No. EP18853365, dated Feb. 1, 2023, 7 pages.
European Search Report and Written Opinion dated Jun. 12, 2018 for EP Application No. 158720441, 5 pages.
European Search Report dated Oct. 16, 2019 for EP Application No. 17763876.4, 11 pages.
European Search Report for EP15838477.6 dated Mar. 5, 2018, 5 pages.
Extended European Search Report for App. No. EP18853365.7, dated May 4, 2021, 7 pages.
Extended European Search Report for App. No. EP18890927.9, dated Jul. 27, 2021, 7 pages.
Extended European Search Report for Application No. EP17819487.4, dated Feb. 4, 2020, 7 pages.
Extended European Search Report for Application No. EP19200585.8, dated Feb. 28, 2020, 8 pages.
Extended European Search Report issued in App. No. EP22185127, dated Dec. 15, 2022, 9 pages.
Extended European Search Report issued in App. No. EP23174959, dated Oct. 9, 2023, 10 pages.
Office Action (Non-Final Rejection) dated Mar. 16, 2026 for U.S. Appl. No. 18/193,265 (pp. 1-21).
English language translation of office action for family member Japanese Patent Application JP2025-526704 dated Jun. 2, 2026.
European search report for EP Application No. 22845557.2, sent May 12, 2025.
Office action for family member Australian Patent Application 2023380290, dated Apr. 13, 2026.
Office Action (Final Rejection) dated Aug. 25, 2026 for U.S. Appl. No. 18/193,265 (pp. 1-20).

* cited by examiner

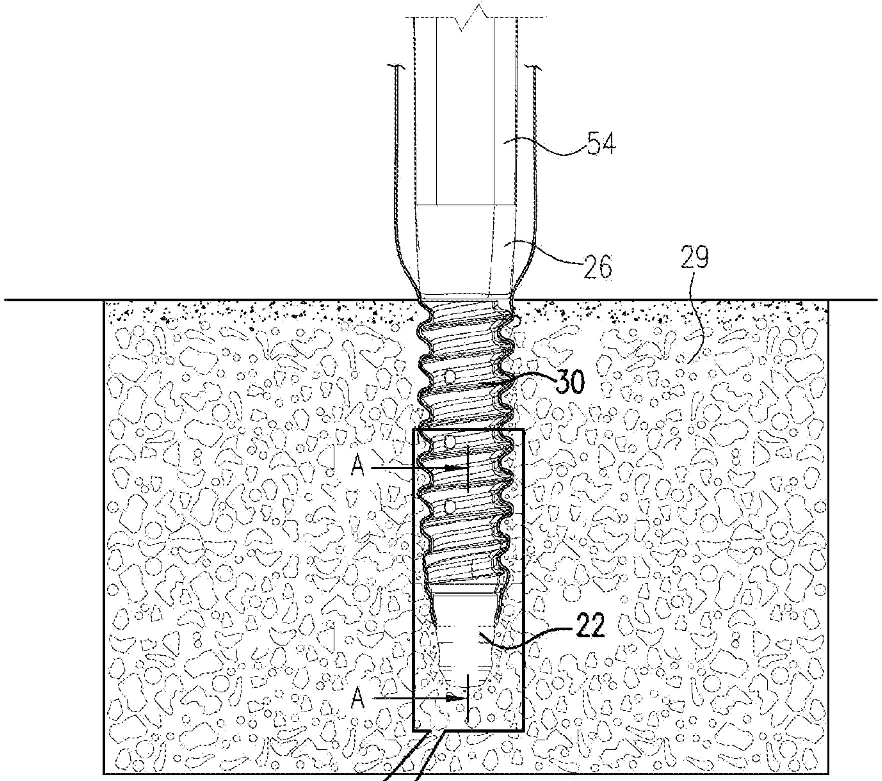
FIG. 2E
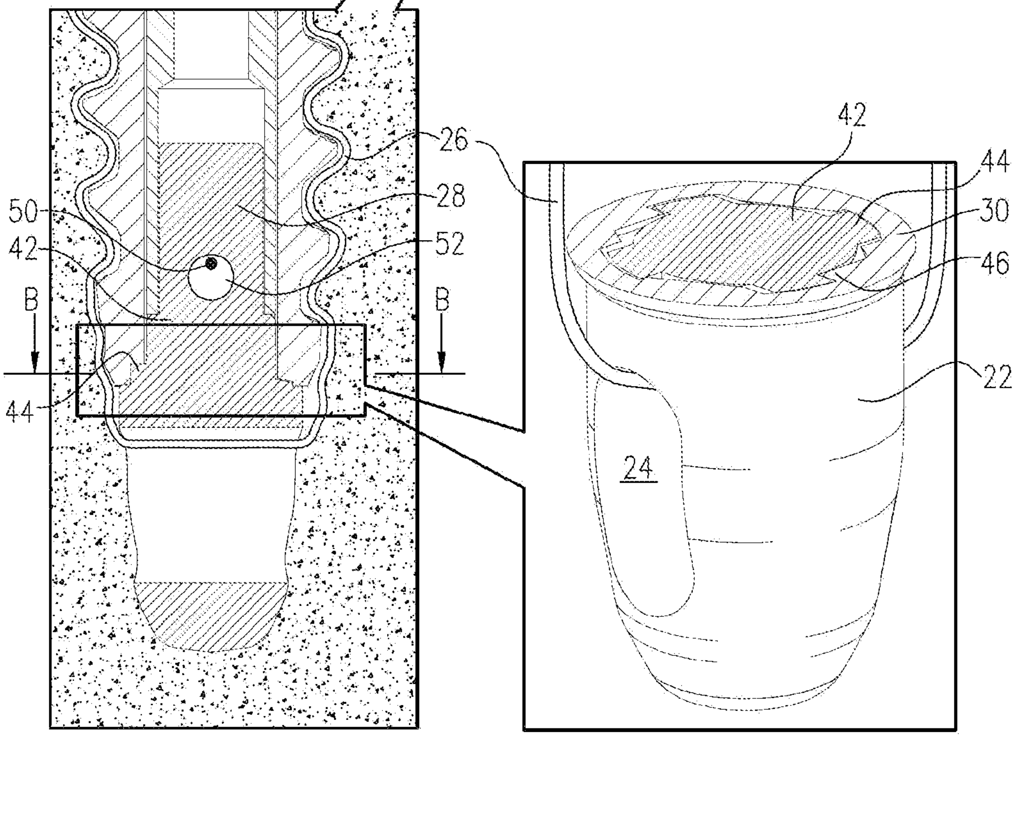

NON-SWIVEL SUTURE ANCHOR FOR KNOTLESS FIXATION OF TISSUE

FIELD OF EMBODIMENTS OF THE INVENTION

The present invention relates to medical apparatus and methods, and specifically to apparatus and methods for securing soft tissue to bone.

BACKGROUND

Grafts are typically secured to bone via sutures. Using traditional methods, the sutures are knotted by the surgeon performing the procedure. More recently, suture anchor devices have been developed for securing soft tissue to bone in a manner that does not require the surgeon to tie suture knots to secure the tissue to the bone. Some such devices include a tip component that defines an eyelet for holding a suture within a pilot hole. The suture is secured into the hole by inserting the eyelet into bone and advancing a plug, such as a cannulated screw, over a shaft of the eyelet.

SUMMARY OF EMBODIMENTS

For some applications of the present invention, a non-swivel suture anchor is configured to secure soft tissue to the bone in a manner that does not require the surgeon to tie suture knots to secure the tissue to the bone. Typically, the non-swivel suture anchor includes a tip component, which is configured to hold a suture within a pilot hole in bone. For some applications, the tip component defines an eyelet. Typically, the eyelet is a closed aperture and the suture is a suture strand that is attached to a graft. For some applications, the eyelet is not a closed aperture. For example, the eyelet may define a portion of a circle, a portion of an ellipse, and/or a forked shape that is configured to hole the suture within the pilot hole. For some applications, the non-swivel suture anchor includes a plug component, which is configured to secure the tip component within the pilot hole by being advanced into and thereby plugging the pilot hole.

The term "non-swivel" is used herein to denote a suture anchor that is configured such that the tip component of the suture anchor is unable to swivel with respect to the plug component of the suture anchor, at least when the plug component is axially engaged with the tip component.

Typically, the plug component is a cannulated screw, which is configured to secure the tip component within the pilot hole by being screwed into the pilot hole to thereby plug the pilot hole. The cannulated screw typically defines a lumen therethrough.

For some applications, the tip component defines a widened end portion toward a first end of the tip component, which is configured to be advanced to the bottom of the pilot hole. The widened end portion typically defines the eyelet, through which the suture is threaded. Typically, the tip component includes a shaft, which extends axially from the widened end portion of the tip component toward a second end of the tip component (which is configured to be placed closer to the top of the pilot hole). The cannulated screw is typically advanced over the shaft of the tip component, such that the shaft is disposed within the lumen of the cannulated screw. The cannulated screw is typically advanced axially until the end of the cannulated screw contacts an upper end of the widened end portion of the shaft. At this point, the cannulated screw is typically unable to advance further axially relative the tip component, due to widened end portion being wider than the lumen defined by the cannulated screw. As such, at this point in the axial advancement of the cannulated screw relative to the tip component, the cannulated screw may be considered to be axially engaged with the tip component.

For some applications, along a region of the shaft that is adjacent to the widened end portion, the shaft defines a widened shaft portion, which is widened relative the rest of the shaft (but typically narrower than the widened end portion). Typically, the widened shaft portion is sized such that when the cannulated screw is advanced over the widened shaft portion, the inner surface of the cannulated screw engages the widened shaft portion. Further typically, the widened shaft portion is sized such that when the cannulated screw is advanced over the widened shaft portion, the widened shaft portion tightly fits within the inner surface of the cannulated screw.

Typically, the tip component is more securely anchored within the cannulated screw due to the inner surface of the cannulated screw engaging the widened shaft portion, relative to if the tip component did not define the widened shaft portion, ceteris paribus. Further typically, the tip component is more securely anchored within the cannulated screw because the widened shaft portion centers the tip component with respect to the cannulated screw, thereby maintaining the axial orientation of the tip component within the bone (even in the presence of asymmetrical pull-out forces exerted by one or more of the sutures).

For some applications, once the cannulated screw is advanced over the widened shaft portion, the tip component is unable to swivel with respect to the cannulated screw, due to the inner surface of the cannulated screw engaging the widened shaft portion. Alternatively, once the cannulated screw is advanced over the widened shaft portion, the tip component is less able to swivel freely with respect to the cannulated screw than it was before this point in its advancement, due to the inner surface of the cannulated screw engaging the widened shaft portion. For some applications, even when the cannulated screw is advanced over the widened shaft portion, the tip component is able to swivel freely with respect to the cannulated screw. (For some applications, when the cannulated screw is advanced over the widened shaft portion, the tip component is unable to swivel freely with respect to the cannulated screw due to tip teeth and screw teeth engaging each other, as described hereinbelow. For some such applications, even when the cannulated screw is partially advanced over the widened shaft portion, the tip component is able to swivel freely with respect to the cannulated screw.)

For some applications, the tip component defines one or more tip teeth proximate to the widened end portion. Typically, a plurality of teeth are arranged circumferentially around the shaft of the tip component. For applications in which the tip component includes a widened shaft portion (as described above), the teeth are typically arranged around the widened shaft portion. For some applications, at the end of the lumen of the cannulated screw, the cannulated screw defines one or more screw teeth, which are shaped so as to engage the tip teeth defined by the tip component. Typically, a plurality of screw teeth are arranged circumferentially around the lumen of the cannulated screw. When the cannulated screw is proximate to the widened end portion of the tip component, the tip teeth and screw teeth typically engage each other, such that the tip component is unable to swivel with respect to the cannulated screw. For some applications, the tip teeth and screw teeth have ramped surfaces that are configured to engage each other, such that the tip component is unable to swivel with respect to the cannulated screw.

There is therefore provided, in accordance with some applications of the present invention, apparatus for securing a suture to a bone, the apparatus including:

a non-swivel suture anchor, including:

a tip component configured to be advanced into a hole within the bone, the tip component including:

a widened end portion that defines an eyelet that is configured to receive the suture;

a shaft that projects axially from the widened end portion, the shaft defining a widened shaft portion proximate to the widened end portion, the widened shaft portion being wider a remainder of the shaft and being narrower than the widened end portion; and a cannulated screw configured to secure the tip component within the hole within the bone, the cannulated screw defining a lumen therethrough that is sized such that as the cannulated screw is advanced over the widened shaft portion, an inner surface of the cannulated screw engages the widened shaft portion.

In some applications, the tip component is configured to be more securely anchored within the cannulated screw due to the inner surface of the cannulated screw engaging the widened shaft portion, relative to if the tip component did not define the widened shaft portion.

In some applications, the widened shaft portion is configured to center the tip component with respect to the cannulated screw, thereby maintaining axial orientation of the tip component within the bone.

In some applications, the widened shaft portion is configured such that once the cannulated screw is advanced over the widened shaft portion, the tip component is unable to swivel with respect to the cannulated screw, due to the inner surface of the cannulated screw engaging the widened shaft portion.

In some applications, the widened shaft portion is configured such that once the cannulated screw is advanced over the widened shaft portion, the tip component becomes less able to swivel with respect to the cannulated screw, due to the inner surface of the cannulated screw engaging the widened shaft portion.

In some applications:

the tip component further includes one or more tip teeth disposed circumferentially around the shaft;

the cannulated screw further includes one or more screw teeth that are arranged circumferentially within the lumen, and the tip teeth and the screw teeth are configured to engage each other, such that when they are engaged the cannulated screw is not swivelable with respect to the tip component.

In some applications, the widened shaft portion is sized such that when the cannulated screw is advanced over the widened shaft portion, the widened shaft portion tightly fits within the inner surface of the cannulated screw.

In some applications, a difference between a diameter of the widened shaft portion and a diameter defined by the inner surface of the cannulated screw is less than 0.5 mm.

In some applications, the difference between the diameter of the widened shaft portion and the diameter defined by the inner surface of the cannulated screw is less than 0.4 mm.

In some applications, the difference between the diameter of the widened shaft portion and the diameter defined by the inner surface of the cannulated screw is less than 0.2 mm.

In some applications, the difference between the diameter of the widened shaft portion and the diameter defined by the inner surface of the cannulated screw is less than 0.1 mm.

In some applications, the inner surface of the cannulated screw has a polygonal shape, and a difference between a diameter of the widened shaft portion and a distance between opposing edges of the polygon defined by inner surface of the cannulated screw is less than 0.5 mm.

In some applications, the difference between the diameter of the widened shaft portion and the distance between opposing edges of the polygon defined by inner surface of the cannulated screw is less than 0.4 mm.

In some applications, the difference between the diameter of the widened shaft portion and the distance between opposing edges of the polygon defined by inner surface of the cannulated screw is less than 0.2 mm.

In some applications, the difference between the diameter of the widened shaft portion and the distance between opposing edges of the polygon defined by inner surface of the cannulated screw is less than 0.1 mm.

In some applications, the tip component includes a fiber-reinforced biocomposite material including a polymer and one or more reinforcing fibers.

In some applications, the cannulated screw includes a fiber-reinforced biocomposite material including a polymer and one or more reinforcing fibers.

In some applications, at least some of the reinforcing fibers at least partially encircle the eyelet.

In some applications, between 8,000 and 20,000 of the reinforcing fibers at least partially encircle the eyelet.

There is further provided, in accordance with some applications of the present invention, apparatus for securing a suture to a bone, the apparatus including:

a non-swivel suture anchor, including:

a tip component configured to be advanced into a hole within the bone, the tip component including:

a widened end portion that defines an eyelet that is configured to receive the suture;

a shaft that projects axially from the widened end portion;

and one or more tip teeth disposed circumferentially around the shaft; and a cannulated screw configured to secure the tip component within the hole within the bone, the cannulated screw defining a lumen therethrough and defining one or more screw teeth that are arranged circumferentially within the lumen, the tip teeth and the screw teeth being configured to engage each other, such that when they are engaged the tip component is not swivelable with respect to the cannulated screw.

In some applications, the tip teeth and screw teeth have ramped surfaces that are configured to engage each other.

In some applications, the tip component includes between 2 and 10 teeth and the cannulated screw includes between 2 and 10 teeth.

In some applications, the tip component includes between 2 and 6 teeth and the cannulated screw includes between 2 and 6 teeth.

In some applications:

the shaft of the tip component defines a widened shaft portion proximate to the widened end portion, the widened shaft portion being narrower than the widened end portion and being wider than a remainder of the shaft, and the lumen of the cannulated screw is sized such that as the cannulated screw is advanced over the widened shaft portion, an inner surface of the cannulated screw engages the widened shaft portion.

In some applications, the tip teeth are disposed circumferentially around the widened shaft portion.

In some applications, the tip component is configured to be more securely anchored within the cannulated screw due to the inner surface of the cannulated screw engaging the widened shaft portion, relative to if the tip component did not define the widened shaft portion.

In some applications, the widened shaft portion is configured to center the tip component with respect to the cannulated screw, thereby maintaining axial orientation of the tip component within the bone.

In some applications, the widened shaft portion is configured such that once the cannulated screw is advanced over the widened shaft portion, the tip component is unable to swivel with respect to the cannulated screw, due to the inner surface of the cannulated screw engaging the widened shaft portion.

In some applications, the widened shaft portion is configured such that once the cannulated screw is advanced over the widened shaft portion, the tip component becomes less able to swivel with respect to the cannulated screw, due to the inner surface of the cannulated screw engaging the widened shaft portion.

In some applications, the widened shaft portion is sized such that when the cannulated screw is advanced over the widened shaft portion, the widened shaft portion tightly fits within the inner surface of the cannulated screw.

In some applications, a difference between a diameter of the widened shaft portion and a diameter defined by the inner surface of the cannulated screw is less than 0.5 mm.

In some applications, the inner surface of the cannulated screw has a polygonal shape, and a difference between a diameter of the widened shaft portion and a distance between opposing edges of the polygon defined by inner surface of the cannulated screw is less than 0.5 mm.

In some applications, the tip component includes a fiber-reinforced biocomposite material including a polymer and one or more reinforcing fibers.

In some applications, the cannulated screw includes a fiber-reinforced biocomposite material including a polymer and one or more reinforcing fibers.

In some applications, at least a portion of the reinforcing fibers at least partially encircle the eyelet.

In some applications, between 8,000 and 20,000 of the reinforcing fibers at least partially encircle the eyelet.

There is further provided, in accordance with some applications of the present invention, a method including:

- securing a suture to a bone, using a non-swivel suture anchor, by:
  - creating a hole in the bone;
  - inserting the suture into an eyelet of a tip component of the non-swivel suture anchor;
  - advancing the tip component into the hole, the tip component including:
    - a widened end portion that defines the eyelet, and
    - a shaft that projects axially from the widened end portion, the shaft defining a widened shaft portion proximate to the widened end portion, the widened shaft portion being wider a remainder of the shaft and being narrower than the widened end portion; and
  - securing the tip component within the hole by advancing a cannulated screw over the shaft of the tip component, the cannulated screw defining a lumen therethrough that is sized such that as the cannulated screw is advanced over the widened shaft portion, the inner surface of the cannulated screw engages the widened shaft portion.

There is further provided, in accordance with some applications of the present invention, a method including:

- securing a suture to a bone, using a non-swivel suture anchor, by:
  - creating a hole in the bone;
  - inserting the suture into an eyelet of a tip component of the non-swivel suture anchor;
  - advancing the tip component into the hole, the tip component including:
    - a widened end portion that defines the eyelet,
    - a shaft that projects axially from the widened end portion, and
    - and one or more tip teeth disposed circumferentially around the shaft; and
  - securing the tip component within the pilot hole by advancing a cannulated screw over the shaft of the tip component, the cannulated screw defining a lumen therethrough and defining one or more screw teeth that are arranged circumferentially within the lumen,
  - advancing the cannulated screw over the shaft of the tip component includes causing the tip teeth and the screw teeth to engage each other, such that the tip component is not swivelable with respect to the cannulated screw.

The present invention will be more fully understood from the following detailed description of applications thereof, taken together with the drawings, in which:

BRIEF DESCRIPTION OF THE DRAWINGS

FIGS. 2A, 2B, 2C, 2D, 2E, and 2F are schematic illustrations of respective steps of a procedure in which a suture is secured to bone, in accordance with some applications of the present invention.

DETAILED DESCRIPTION OF EMBODIMENTS

Figure 1:
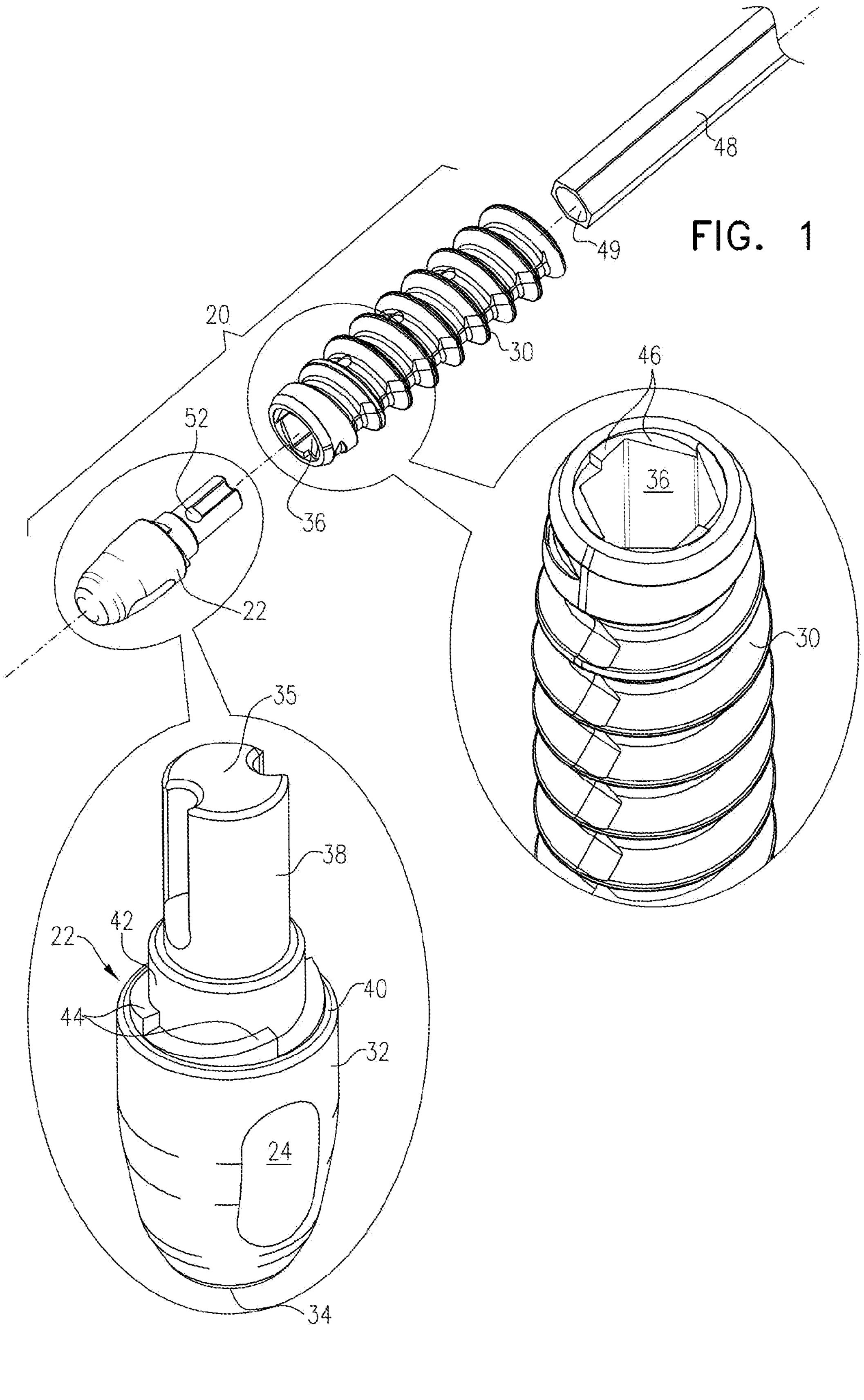
FIG. 1 is a schematic illustration of a non-swivel suture anchor, in accordance with some applications of the present invention.

Reference is now made to FIG. 1, which is a schematic illustration of a non-swivel suture anchor 20, in accordance with some applications of the present invention. For some applications, the suture anchor is configured to secure soft tissue to the bone in a manner that does not require the surgeon to tie suture knots to secure the tissue to the bone. Typically, the non-swivel suture anchor includes a tip component 22 that defines an eyelet 24, which is configured to hold a suture 26 within a pilot hole 28 in bone 29 (suture 26, pilot hole 28, and bone 29 all shown in FIGS. 2A-F). Typically, the eyelet is a closed aperture and the suture is a suture strand that is attached to a graft (not shown). For some applications (not shown), the eyelet is not a closed aperture. For example, the eyelet may define a portion of a circle, a portion of an ellipse, and/or a forked shape that is configured to hole the suture within the pilot hole.

For some applications, the non-swivel suture anchor includes a plug component, which is configured to secure the tip component within the pilot hole by being advanced into and thereby plugging the pilot hole. Typically, the plug component is a cannulated screw 30 (as shown), which is configured to secure the tip component within the pilot hole by being screwed into the pilot hole to thereby plug the pilot hole. Cannulated screw 30 typically defines a lumen 36 therethrough.

For some applications, tip component 22 defines a widened end portion 32 toward a first end 34 of the tip component, which is configured to be advanced to the bottom of the pilot hole. The widened end portion typically defines eyelet 24, through which the suture is threaded. Typically, the tip component includes a shaft 38, which extends axially from the widened end portion of the tip component toward a second end 35 of the tip component (which is configured to be placed closer to the top of the pilot hole). The cannulated screw is typically advanced over shaft 38 of the tip component, such that the shaft is disposed within lumen 36 of the cannulated screw. The cannulated screw is typically advanced axially until the end of the cannulated screw contacts an upper end 40 of widened end portion 32. At this point the cannulated screw is typically unable to advance further axially relative the tip component, due to widened end portion 32 being wider than the lumen defined by the cannulated screw. As such, at this point in the axial advancement of the cannulated screw relative to the tip component, the cannulated screw may be considered to be axially engaged with the tip component.

For some applications, along a region of shaft 38 that is adjacent to widened end portion 32, the shaft defines a widened shaft portion 42, which is widened relative the rest of the shaft (but typically narrower than widened end portion 32). Typically, widened shaft portion 42 is sized such that when cannulated screw 30 is advanced over widened shaft portion 42, the inner surface of the cannulated screw engages widened shaft portion 42. Further typically, widened shaft portion 42 is sized such that when cannulated screw 30 is advanced over widened shaft portion 42, the widened shaft portion tightly fits within the inner surface of the cannulated screw. For example, the difference between the diameter of widened shaft portion 42 and the nominal diameter defined by the inner surface of the cannulated screw may be less than 0.5 mm, less than 0.4 mm, less than 0.2 mm, or less than 0.1 mm (for example, the difference may be 0.01 mm-0.5 mm, e.g., 0.02 mm-0.4 mm, 0.04-0.2 mm, or 0.05-0.1 mm). (It is noted that in some cases, the inner surface of the cannulated screw has a polygonal (e.g., a hexagonal) shape, in which case the diameter of the above-described ranges are applicable to the difference between (a) the diameter of widened shaft portion 42, and (b) the distance between opposing edges of the polygon defined by inner surface of the cannulated screw.

Typically, tip component 22 is more securely anchored within cannulated screw 30 due to the inner surface of the cannulated screw engaging widened shaft portion 42, relative to if the tip component did not define widened shaft portion 42, ceteris paribus. Further typically, the tip component is more securely anchored within the cannulated screw because the widened shaft portion centers the tip component with respect to the cannulated screw, thereby maintaining the axial orientation of the tip component within the bone (even in the presence of asymmetrical pull-out forces exerted by one or more of sutures 26).

For some applications, once cannulated screw 30 is advanced over widened shaft portion 42, tip component 22 is unable to swivel with respect to cannulated screw 30, due to the inner surface of the cannulated screw engaging widened shaft portion 42. Alternatively, once cannulated screw 30 is advanced over widened shaft portion 42, the tip component is less able to swivel freely with respect to the cannulated screw than it was before this point in its advancement, due to the inner surface of the cannulated screw engaging widened shaft portion 42. For some applications, even when the cannulated screw is advanced over widened shaft portion 42, the tip component is able to swivel freely with respect to the cannulated screw. (For some applications, when the cannulated screw is advanced over the widened shaft portion, the tip component is unable to swivel freely with respect to the cannulated screw due to tip teeth and screw teeth engaging each other, as described hereinbelow. For some such applications, even when the cannulated screw is partially advanced over the widened shaft portion, the tip component is able to swivel freely with respect to the cannulated screw.)

For some applications, tip component 22 defines one or more tip teeth 44, which are typically proximate to widened end portion 32. For example, the tip component 22 may define 2-10, e.g., 2-6 (e.g., 4) tip teeth 44. Typically, a plurality of teeth are arranged circumferentially around shaft 38 of the tip component. For applications in which the tip component includes widened shaft portion 42 (as described in the above paragraph), the teeth are typically arranged around widened shaft portion 42, as shown. For some applications, at the end of lumen 36 of cannulated screw 30, the cannulated screw defines one or more screw teeth 46, which are shaped so as to engage tip teeth 44 defined by the tip component. For example, the cannulated screw may define 2-10, e.g., 2-6 (e.g., 4) screw teeth 46. Typically, a plurality of screw teeth 46 are arranged circumferentially around lumen 36 of cannulated screw 30. When the cannulated screw is proximate to widened end portion 32 of tip component 22, tip teeth 44 and screw teeth 46 typically engage each other, such that tip component 22 is unable to swivel with respect to cannulated screw 30. For some applications, tip teeth 44 and screw teeth 46 have ramped surfaces that are configured to engage each other, such that tip component 22 is unable to swivel with respect to cannulated screw 30.

As noted above, typically, the tip component is more securely anchored within the cannulated screw because the widened shaft portion centers the tip component with respect to the cannulated screw, thereby maintaining the axial orientation of the tip component within the bone (even in the presence of asymmetrical pull-out forces exerted by one or more of sutures 26). Also as noted above, for some applications, the engagement of the inner surface of the cannulated screw 30 with widened shaft portion 42 is such that at least when the cannulated screw is axially engaged with the tip component (i.e., when the cannulated screw has been advanced until the end of the cannulated screw contacts an upper end 40 of widened end portion 32), tip component 22 is unable to swivel with respect to cannulated screw 30. Alternatively or additionally, the engagement of tip teeth 44 and screw teeth 46 is such that at least when the cannulated screw is axially engaged with the tip component (i.e., when the cannulated screw has been advanced until the end of the cannulated screw contacts an upper end 40 of widened end portion 32), tip component 22 is unable to swivel with respect to cannulated screw 30. In general, the inventors of the present application have found that the aforementioned features result in the tip component being more securely anchored in place within the pilot hole (and the suture thereby being more securely anchored within the pilot hole) relative to using a suture anchor that does not include the above-described features. This is described in further detail hereinbelow with respect to Example 1.

It is noted that, although non-swivel suture anchor 20 has been described as including two features for preventing or reducing swiveling of tip component 22 with respect to cannulated screw 30 (i.e., widened shaft portion 42, as well as tip teeth 44 and screw teeth 46), the scope of the present invention includes a non-swivel suture anchor 20 that includes only one of the features for preventing or reducing swiveling of the tip component with respect to the cannulated screw and not the other one.

As described hereinabove, cannulated screw 30 is typically configured to secure the tip component within the pilot hole by being screwed into the pilot hole to thereby plug the pilot hole. For some applications, a rotation rod 48 is used to rotate the cannulated screw in order to screw the cannulated screw into the pilot hole, as described in further detail hereinbelow with reference to FIGS. 2A-F. Typically, the rotation rod has a cross-sectional shape that conforms with an inner cross-sectional shape the defines the lumen of the cannulated screw, such that the rotation rod engages the internal surfaces of the cannulated screw. For example, the rotation rod may have a polygonal (e.g., a hexagonal shape) and the inner cross-sectional shape that defines the lumen of the cannulated screw may also be polygonal (e.g., hexagonal, as shown). Alternatively, other shapes may be used. Further alternatively or additionally, other methods may be used for rotating the canulated interference screw.

Reference is now made to FIGS. 2A, 2B, 2C, 2D, 2E, and 2F, which are schematic illustrations of respective steps of a procedure in which a suture 26 is secured to bone 29, in accordance with some applications of the present invention.

Figure 2A:
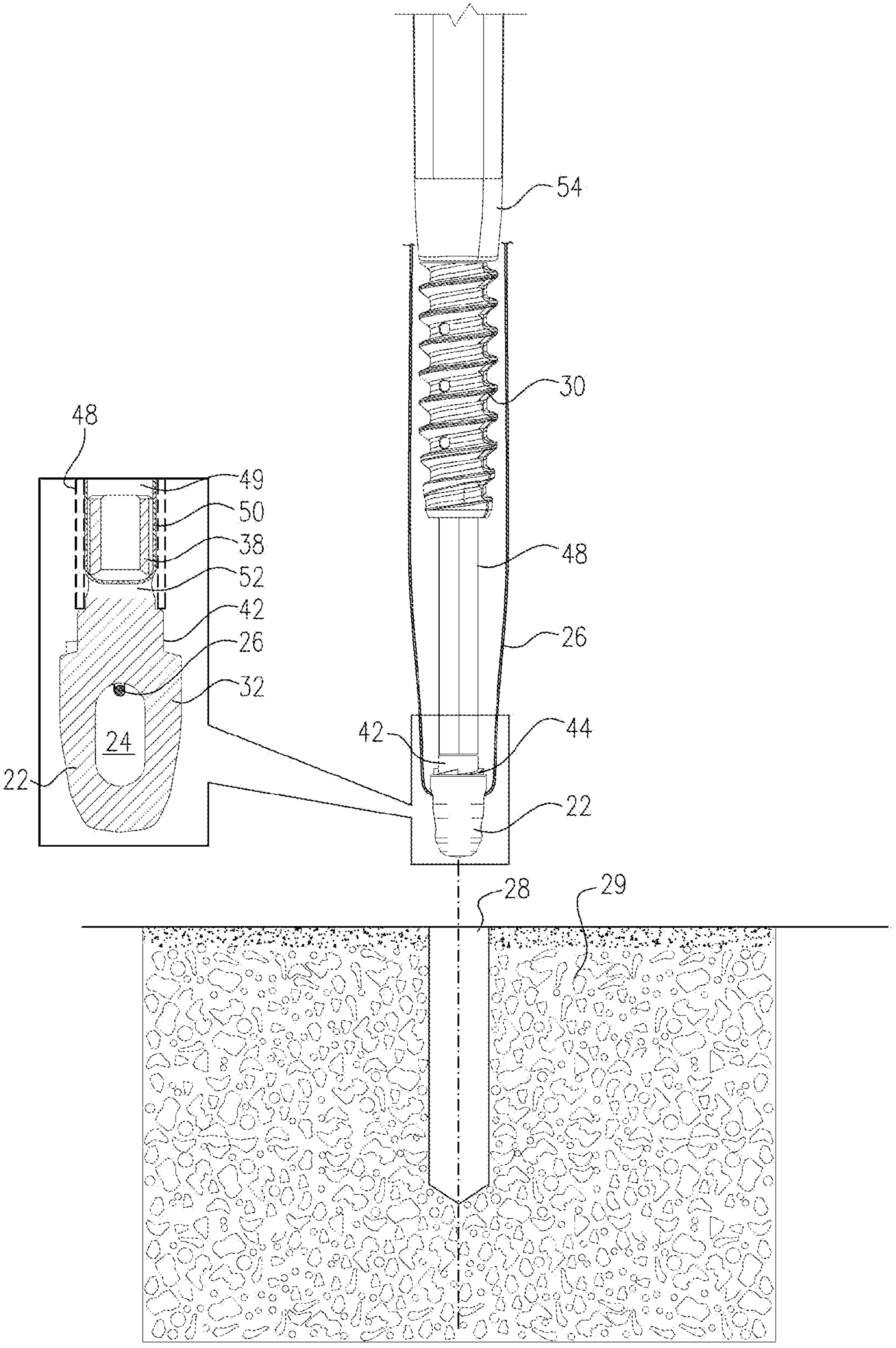

Typically, in a first step, pilot hole 28 is drilled into bone 29. FIG. 2A shows bone 29 with pilot hole having already been drilled, and with non-swivel suture anchor 20 and suture 26 prepared for insertion into the pilot hole. For some applications, pilot hole 28 is equal to the total length of the suture anchor 20. Alternatively, the pilot hole is shorter than the total length of the suture anchor 20, e.g., up to half of the total length of the suture anchor. As shown, suture 26 is threaded though eyelet 24 of tip component 22. Cannulated screw 30 is mounted on rotation rod 48 above the tip component, with an axial gap between the cannulated screw and the tip component. For some applications, the length of the gap is approximately equal to the length of the pilot hole.

Typically, rotation rod 48 is cannulated and defines a lumen therethrough. For some applications, the tip component is held at the end of the rotation rod using a stay suture 50, which passes through a stay-suture eyelet 52 (defined by shaft 38 of the tip component) and then passes along the rotation rod lumen. For some applications, the apparatus includes an axial pushing element 54, which is configured to push cannulated screw 30 axially along rotation rod 48, while rotation rod 48 rotates the cannulated screw, as described in further detail hereinbelow.

Figure 2B:
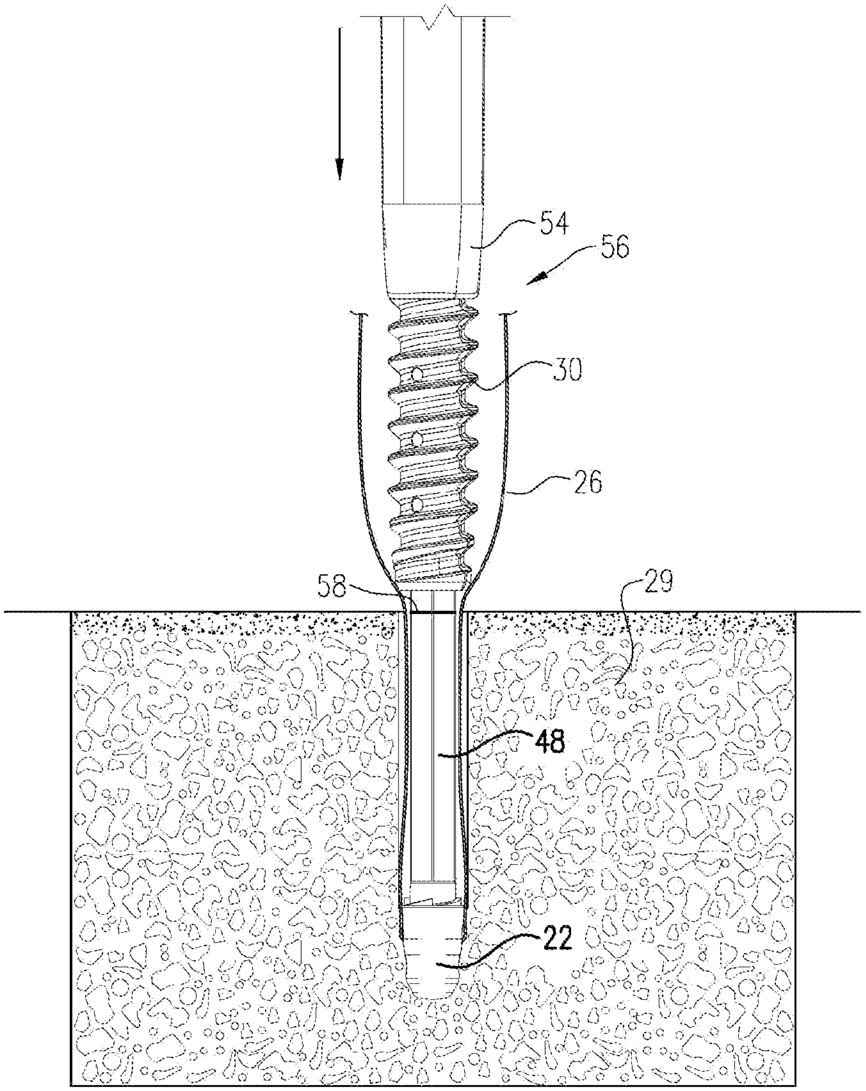

Referring now to FIG. 2B, in a subsequent step, tip component 22 and rotation rod 48 are advanced into the pilot hole. For some applications, rotation rod 48 and axial pushing element 54 comprise portions of a driver 56, and the tip component 22 and rotation rod 48 are advanced into the pilot hole by gently tapping an upper end (not shown) of the driver. For some applications, the rotation rod includes a marking 58 (e.g., a laser-cut marking) to indicate a depth to which to advance the rotation rod into the pilot hole. As noted above, for some applications, the pilot hole is shorter than the total length of the suture anchor 20, e.g., up to half of the total length of the suture anchor. As shown, for such applications, the tip element is advanced into bone 29 to a greater depth than the depth of the pilot hole that was drilled. Typically, this is possible because cancellous bone tissue is spongy. Further typically, this results in the tip component being more securely anchored in place within the pilot hole (and the suture thereby being more securely anchored within the pilot hole) relative to the tip element is advanced into bone 29 only as far as the depth of the pilot hole that was drilled.

Figure 2C:
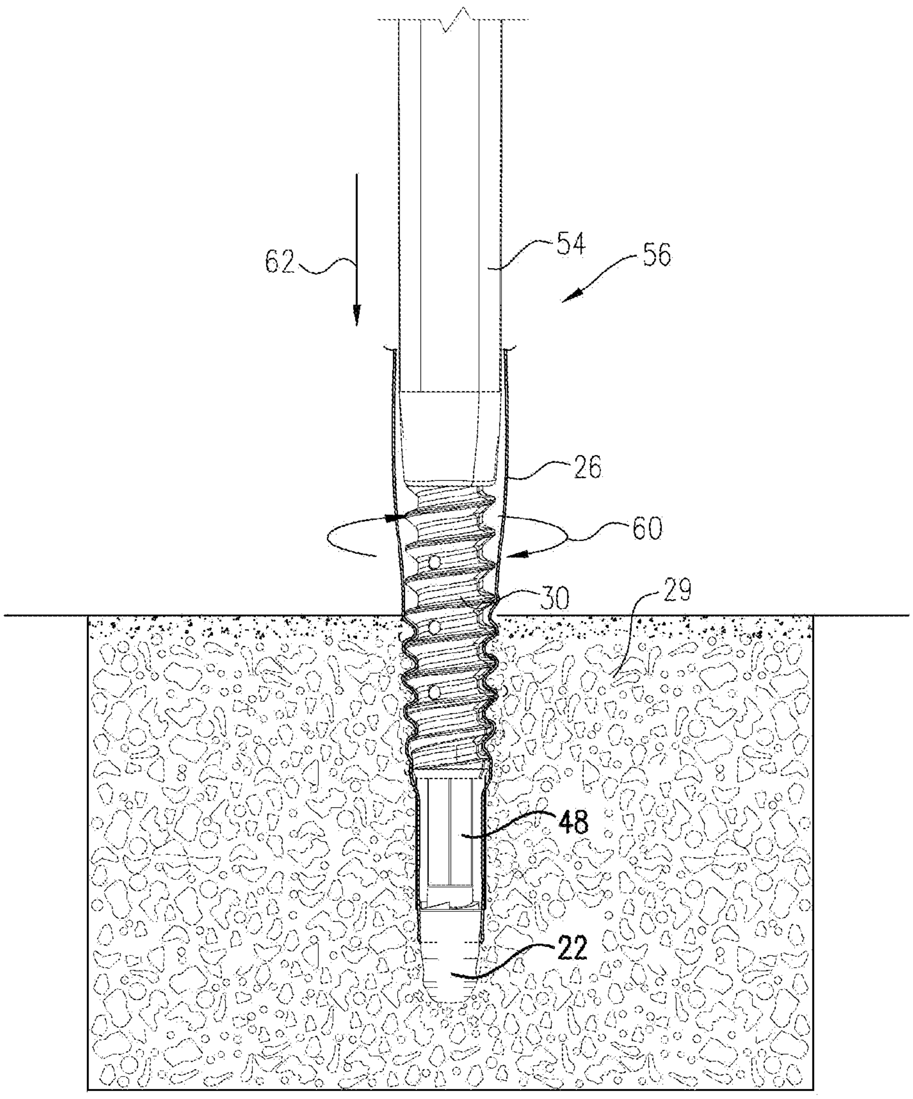
Figure 2D:
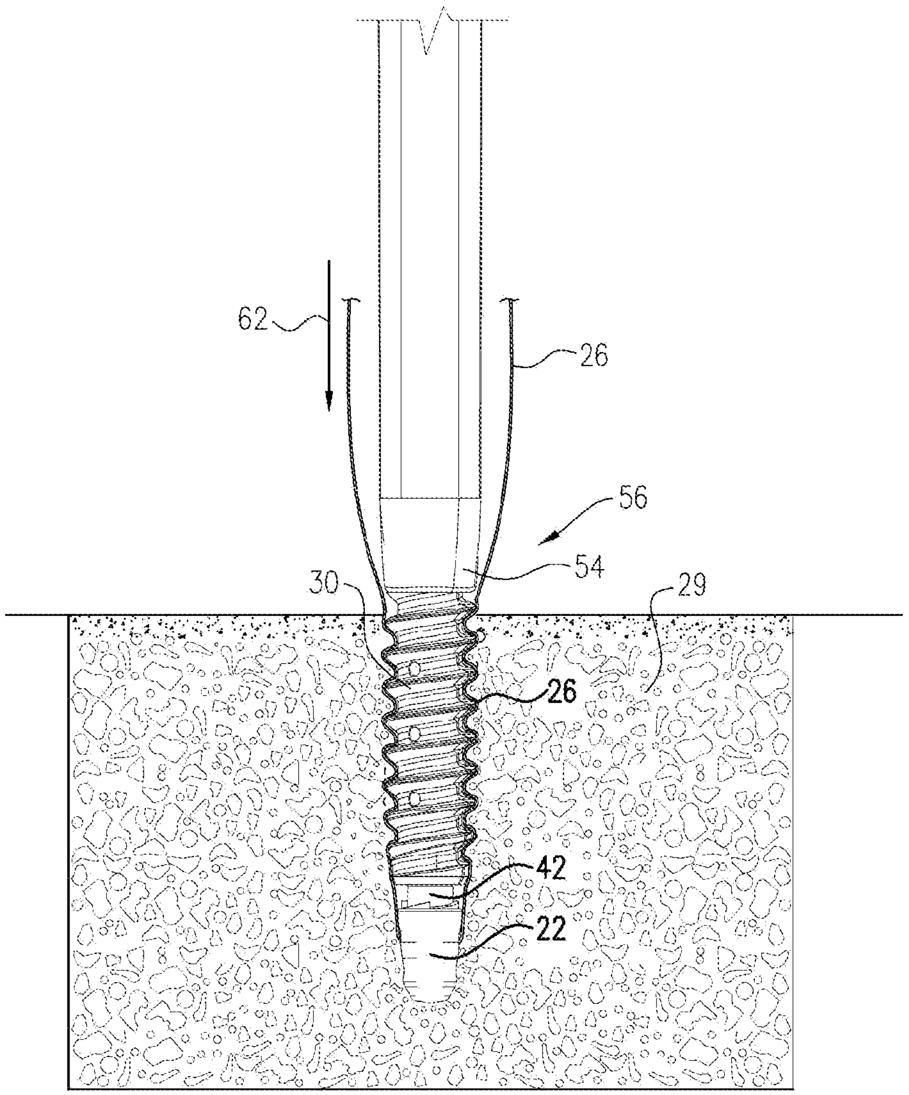

Referring now to FIGS. 2C and 2D, typically, the cannulated screw is screwed into the pilot hole by simultaneously (a) rotating rotation rod 48 (as indicated by arrow 60 in FIG. 2C), and (b) pushing cannulated screw 30 axially along rotation rod 48 using axial pushing element 54 (as indicated by arrow 62 in FIGS. 2C and 2D). FIGS. 2C and 2D show respective stages of the advancement of the cannulated screw with respect to the tip component. FIG. 2D shows the cannulated screw just before the lower end of the cannulated screw has been advanced over widened shaft portion 42 of tip component 22.

As shown in the transition from FIG. 2D to FIG. 2E, as the cannulated screw continues to be advanced axially with respect to tip component 22 (a) the inner surface of the cannulated screw engages widened shaft portion 42, and subsequently (b) tip teeth 44 and screw teeth 46 typically engage each other, such that the cannulated screw is unable to swivel with respect to tip component 22. As noted above, for some applications, the engagement of the inner surface of cannulated screw 30 with widened shaft portion 42 is such that the tip component becomes securely anchored within the cannulated screw because the widened portion centers the tip component with respect to the cannulated screw 30, thereby maintaining the axial orientation of the tip component within the bone (even in the presence of asymmetrical pull-out forces exerted by one or more of the active sutures 26). For some applications, the engagement of the inner surface of the cannulated screw 30 with widened shaft portion 42 is such that at least when the cannulated screw is axially engaged with the tip component (i.e., when the cannulated screw has been advanced until the end of the cannulated screw contacts an upper end 40 of widened end portion 32), the tip component is not swivelable with respect to the cannulated screw (or becomes less swivelable with respect to the cannulated screw). Typically, the engagement of tip teeth 44 and screw teeth 46 is such that at least when the cannulated screw is axially engaged with the tip component (i.e., when the cannulated screw has been advanced until the end of the cannulated screw contacts an upper end 40 of widened end portion 32), the tip component is not swivelable with respect to the cannulated screw. In general, the inventors of the present application have found that the aforementioned features result in the tip component being more securely anchored in place within the pilot hole (and the suture thereby being more securely anchored within the pilot hole) relative to using a suture anchor that does not include the above-described features. This is described in further detail hereinbelow with respect to Example 1.

It is again noted that, although non-swivel suture anchor 20 has been described as including two features for preventing or reducing swiveling of the tip component with respect to the cannulated screw (i.e., widened shaft portion 42, as well as tip teeth 44 and screw teeth 46), the scope of the present invention includes a non-swivel suture anchor 20 that includes only one of the features for preventing or reducing swiveling of the tip component with respect to the cannulated screw and not the other one.

Figure 2F:
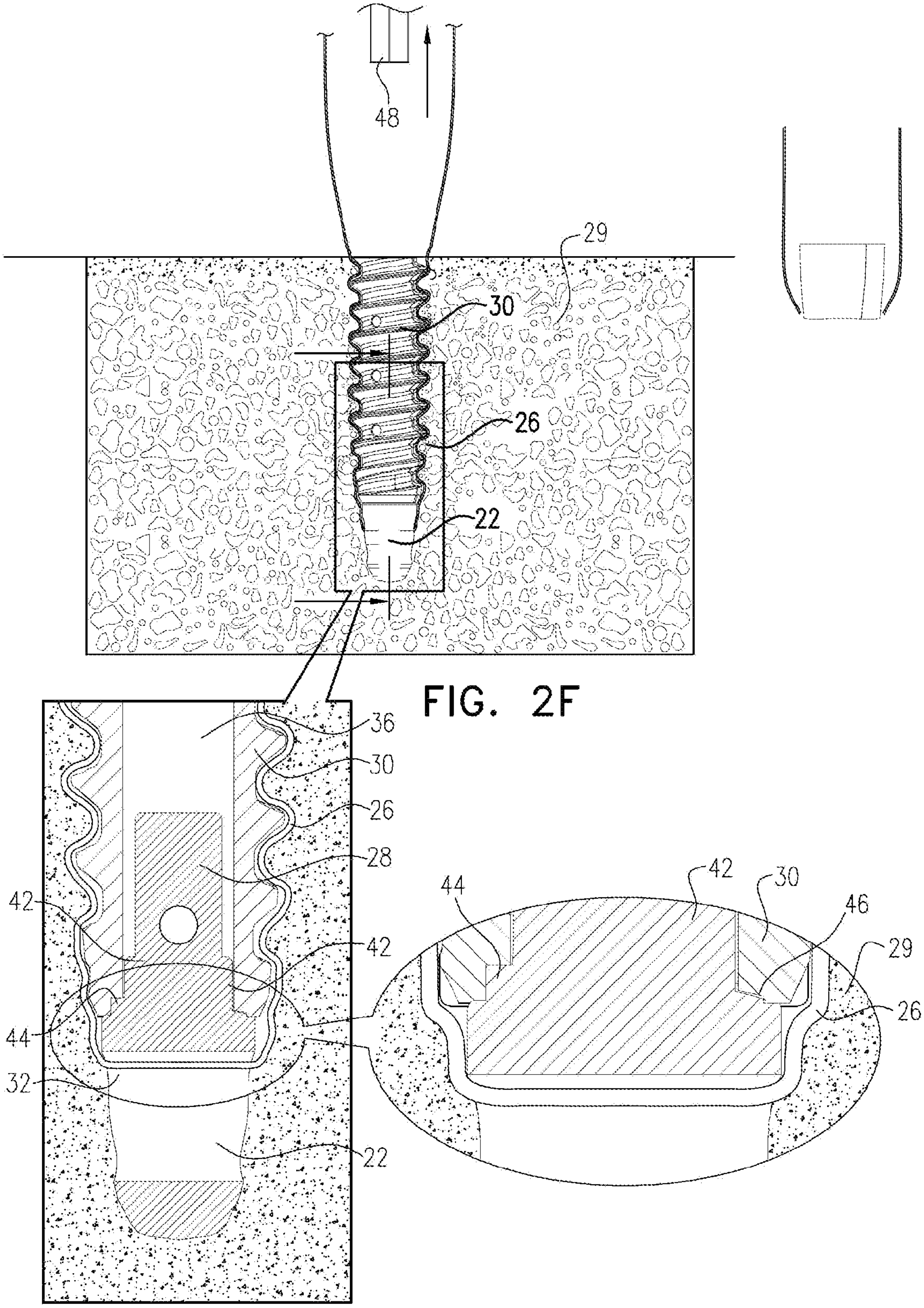

With reference to the transition from FIG. 2E to FIG. 2F, once the cannulated screw is axially engaged with the tip component (i.e., when the cannulated screw has been advanced until the end of the cannulated screw contacts an upper end 40 of widened end portion 32), stay suture 50 is removed from stay-suture eyelet 52, and rotation rod is removed from within lumen 36 of the cannulated screw. Typically, at this stage, tip component 22 is securely anchored in place within the pilot hole (and the suture is thereby anchored within the pilot hole). Further typically, at this stage (as with the previous stage described with reference to FIG. 2E), the tip component is not swivelable with respect to the cannulated screw.

Figure 3:
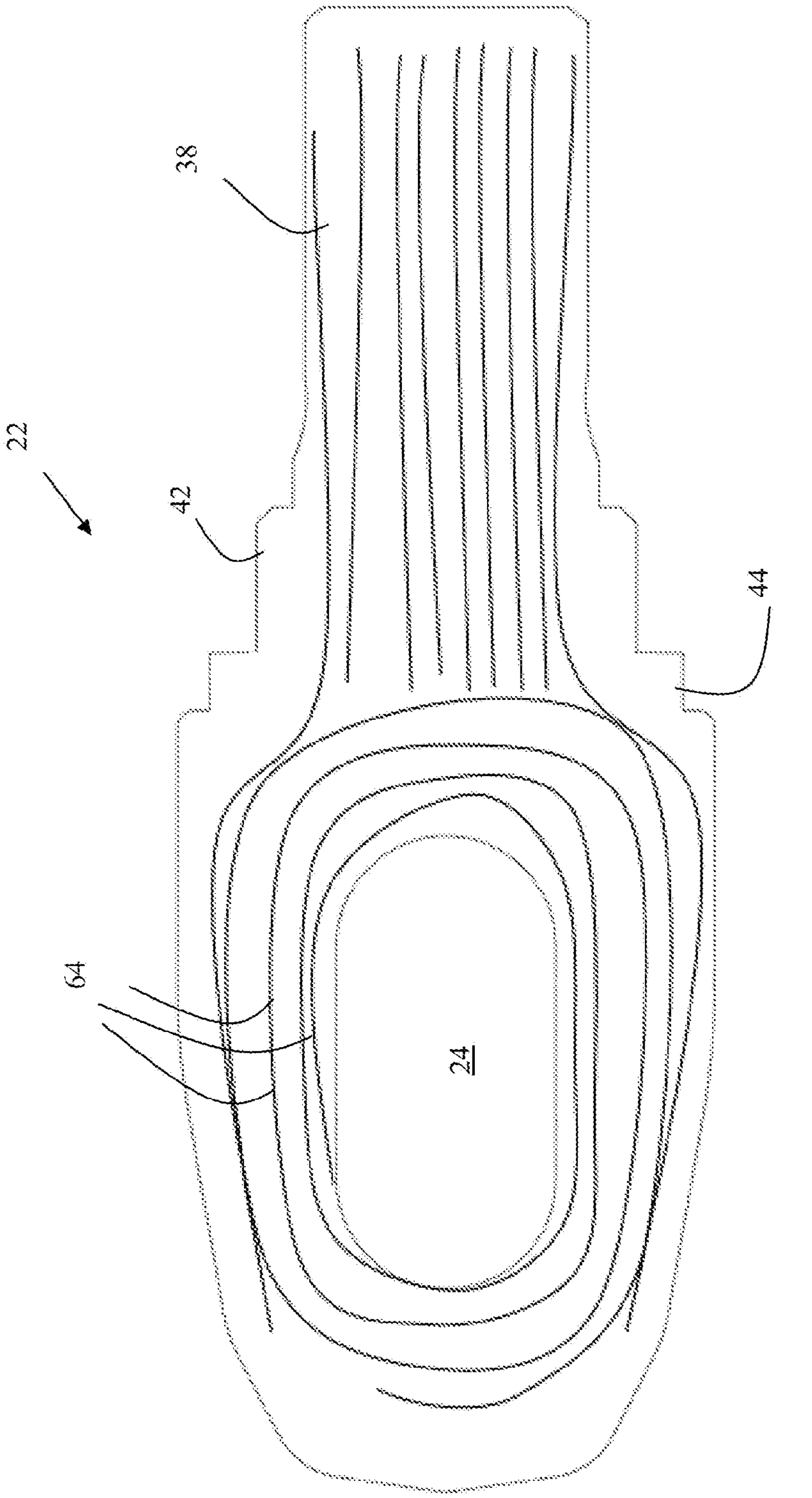
FIG. 3 is a schematic illustration of a tip component of the non-swivel suture anchor that illustrates the orientation of reinforcement fibers within a tip component of the anchor, in accordance with some applications of the present invention.

Reference is now made to FIG. 3, which is a schematic illustration of tip component 22 of non-swivel suture anchor 20 that illustrates the orientation of fibers 64 within the tip component, in accordance with some applications of the present invention. Typically, both cannulated screw 30 and tip component 22 are made of fiber-reinforced biocomposite materials, for example, as described in U.S. Ser. No. 16/637,363, which is the US national phase of WO 19/049062, and which is incorporated herein by reference.

Typically, the biocomposite material composition is comprised of (an optionally bioabsorbable) polymer reinforced by a mineral composition. Further typically, the mineral composition reinforcement is provided by a reinforcing fiber made from the mineral composition. The mineral content of tip component 22 and/or cannulated screw 30 is typically quite high. For some applications, the tip component 22 and/or cannulated screw 30 of non-swivel suture anchor 20 is comprised of a number of biocomposite layers, each layer comprising bioabsorbable polymer reinforced by unidirectional reinforcing fibers. The properties of tip component 22 and/or cannulated screw 30 are typically determined according to the layer composition and structure, and the placement of the layers in regard to the device, for example with regard to layer direction. The fibers may optionally remain discrete but optionally some melting of the polymer may occur to bind the layers together. A biocomposite layer can be defined as a continuous or semi-continuous stratum running through part or all of tip component 22 and/or cannulated screw 30, wherein the layer is comprised of reinforcing fibers that are aligned uni-directionally.

For some applications, within the tip component, the fiber structure is made of continuous fibers 64. Typically, the continuous fibers within the tip component are configured to provide reinforcement to eyelet 24. For example, as shown the eyelet may be reinforced by multiple fibers at least partially encircling the eyelet. The eyelet is typically reinforced by fibers either completely or partially encircling the circumference of the eyelet. In accordance with respective applications, a single fiber may be wrapped multiple times around the eyelet or may be wrapped just once around the eyelet. Each of the multiple fibers encircling the eyelet may similarly encircle the eyelet partially, fully, or even multiple times (i.e. wrapped around). For some applications, the bottom portion of tip component 22 (between the eyelet 24 and the widened shaft portion 42), has an increased density of continuous fiber reinforcement. The number of fibers encircling the eyelet is typically in the range of 8,000 to 20,000. For some applications, stay suture eyelet 52 is reinforced in a similar manner to that shown for eyelet 24, mutatis mutandis.

Typically, reinforcement fibers 64 are comprised of silica-based mineral compound such that reinforcement fiber comprises a bioresorbable glass fiber, which can also be termed a bioglass fiber composite. Mineral composition may alternatively include beta-tri calcium phosphate, calcium phosphate, calcium sulfate, hydroxyapatite, or a bioresorbable glass (also known as bioglass). For some applications, the reinforcing fiber is bound to the bioabsorbable polymer such that the reinforcing effect is maintained for an extended period. Bioresorbable glass fiber may optionally have oxide compositions in the following mol. % ranges:

Na20: 11.0-19.0 mol. %
CaO: 8.0-14.0 mol. %
MgO: 1.5-8.0 mol. %
B203: 0.5-3.0 mol. %
Al203: 0-0.8 mol. %
P203: 0.1-0.8 mol. %
Si02: 65-73 mol. %

And more preferably in the following mol. % ranges:

Na20: 12.0-13.0 mol. %
CaO: 8.0-10.0 mol. %
MgO: 7.0-8.0 mol. %
B203: 1.4-2.0 mol. %
P203: 0.5-0.8 mol. %
Si02: 65-70 mol. %

For some applications, the fibers are present in tip component 22 and/or cannulated screw 30 in either linear or concentric circular layers. Typically, each layer is uniform in the orientation of its fibers. For some applications, the number of layers is constant across tip component 22 and/or cannulated screw 30. Alternatively, the number of layers varies across tip component 22 and/or cannulated screw 30.

Preferably the layers are of thickness 0.05-0.3 mm and more preferably 0.1 mm to 0.18 mm. Preferably the thickness of the layers is constant across tip component 22 and/or cannulated screw 30. Alternatively the thickness of the layers varies across tip component 22 and/or cannulated screw 30.

Preferably the layers are 8-40 fibers thick, and more preferably 8-15 fibers thick. Optionally, each layer is comprised of fibers aligned at the longitudinal axis of the tip component 22 and/or cannulated screw 30, at an angle to the longitudinal axis, or at a negative angle to the longitudinal axis.

Optionally, the differently aligned layers are distributed evenly throughout tip component 22 and/or cannulated screw 30.

Optionally, the diameter of a majority of reinforcing fibers 64 for use tip component 22 and/or cannulated screw 30 is in the range of 1-100 microns. Preferably, fiber diameter is in the range of 1-20 microns. More preferably, fiber diameter is in the range of 4-16 microns, and most preferably in the range of 8-15 microns. Optionally, the average diameter of reinforcing fiber for use within tip component 22 and/or cannulated screw 30 is in the range of 1-100 microns. Preferably, fiber diameter is in the range of 1-20 microns. More preferably, fiber diameter is in the range of 4-16 microns, and most preferably in the range of 8-15 microns.

For some applications, reinforcing fibers are fiber segments inside a polymer matrix. Preferably such fiber segments are, on average, of length 0.5-20 mm, more preferably the fiber segment length is in the range of 1-15 mm, more preferably in the range of 3-10 mm and most preferably in the range of 4-8 mm. Preferably, a majority of reinforcing fiber segments are of length 0.5-20 mm, more preferably the fiber segment length is in the range of 1-15 mm, more preferably in the range of 3-10 and most preferably in the range of 4-8 mm.

Optionally, the reinforcing fibers are continuous fibers. The continuous fibers are preferably longer than 5 mm, more preferably longer than 8 mm, 12 mm, 16 mm, and most preferably longer than 20 mm. Alternatively, or in addition, the reinforcing fiber length can be defined as a function of tip component 22 and/or cannulated screw 30 wherein at least a portion of the reinforcing fibers, and preferably a majority of the reinforcing fibers, are of a continuous length at least 50% the longitudinal length of tip component 22 and/or cannulated screw. Preferably, the portion or majority of the reinforcing fibers are of continuous length at least 60% of the length of tip component 22 and/or cannulated screw 30, and more preferably at least 75% of the length of the tip component 22 and/or cannulated screw 30. Such continuous reinforcing fibers can provide structural reinforcement to a large part of tip component 22 and/or cannulated screw 30.

Optionally, the distance between adjacent reinforcing fibers within a biocomposite layer is in the range of 0.5-50 microns, preferably the distance between adjacent fibers is in the range of 1-30 microns, more preferably in the range of 1-20 microns, and most preferably in the range of 1-10 microns.

Preferably, the weight percentage of the reinforcing fibers (mineral composition) within tip component 22 and/or cannulated screw 30 is in the range of 40-90%, more preferably the weight percentage is in the range of 40%-70%, more preferably in the range of 40%-60%, and even more preferably the weight percentage is in the range of 45%-60%.

Preferably, the volume percentage of reinforcing fibers within the tip component 22 and/or cannulated screw 30 is in the range of 30-90%), more preferably the volume percentage is in the range of 40%-70%.

Optionally, a plurality of fibers within tip component 22 and/or cannulated screw 30 are uni-directionally aligned. Optionally, the aligned fiber segments are, on average, of length 5-12 mm.

The term "Biocomposite" as used herein is a composite material formed by a matrix and a reinforcement of fibers wherein both the matrix and fibers are biocompatible and optionally bioabsorbable. In most cases, the matrix is a polymer resin, and more specifically a synthetic bioabsorbable polymer. The fibers are optionally and preferably of a different class of material (i.e. not a synthetic bioabsorbable polymer), and may optionally comprise mineral, ceramic, cellulosic, or other type of material.

Example 1

As noted above, the inventors of the present application have found that features described herein result in the tip component being more securely anchored in place within the pilot hole (and the suture thereby being more securely anchored within the pilot hole) relative to using a tip component that is fully swivelable with respect to the cannulated screw. This is now described in further detail with reference to an experimental example. This example describes the pull-out testing of non-swivel suture anchors as described herein compared with swivel suture anchors of the same size. This example demonstrates how a suture anchor having a tip component that is unable to swivel upon full advancement of the plug component, and that is generally as described herein, outperforms a suture anchor in which the tip component is fully swivelable with respect to the plug component, in both static and dynamic pull-out testing, both at time zero (following production) and following simulated degradation at multiple time points.

Materials & Methods

Two types of threaded suture anchors were tested, with each having an outer thread diameter of 4.75 mm.

One type of suture anchor was manufactured according to a non-swivel design as described herein. This suture anchor was manufactured from a fiber-reinforced composite comprised of PLDLA 70/30 polymer reinforced with 45-50% w/w continuous mineral fibers. Mineral fibers composition was approximately $Na_2O$ 14%, MgO 5.4%, CaO 9%, $B_2O_3$ 2.3%, $P_2O_5$ 1.5%, and $SiO_2$ 67.8% w/w. Testing samples were manufactured by compression molding of multiple layers of composite material into a mold, with a hexagonal pin insert in the center. Each layer was approximately 0.18 mm thick. The two components of the suture anchor (tip component and screw) were both comprised of fiber-reinforced composite.

The second suture anchor was a commercially-available biocomposite swivel anchor (SwiveLock®, manufactured by Arthrex® (Florida, USA)). This screw component of this anchor is comprised of 85% PLLA and 15%-βtricalcium phosphate while the tip component is comprised of PEEK.

The pull-out forces of both suture anchors were tested by inserting a #2 round suture through the eyelet component of the anchor and then inserting the anchor into a 15 PCF sawbone. After an appropriately sized 16 mm tunnel was drilled into the sawbone surface, the screw component of each anchor was inserted into the tunnel in the sawbone until the screw was flush with the sawbone surface.

For each test, the sawbone was fixed to the bottom of the tensile testing system frame with the samples submerged in DPBS solution and the ends of the suture attached to a 500 N load cell attached to the tensile testing system (MTS Criterion Machine, model 42. Load cell: 500 N, model LSB.502).

For the static tests, the ends of the suture were pulled up at a constant displacement of 5 mm/min. Displacement and load were measured at a sampling rate of 100/second. The test stopped when the sampled load dropped to 50% of the peak load value.

For the dynamic tests, the testing setup was identical except that the ends of the suture were pulled at a force cycling between 100 N minimum force and 180 N maximum force until runout (i.e., failure of the suture anchor).

Testing was conducted initially (time zero) and following simulated in vitro degradation according to modified ASTM F1635 (Standard Test Method for in vitro Degradation Testing of Hydrolytically Degradable Polymer Resins and Fabricated Forms for Surgical Implants, http://www.astma org/Standards/F1635.htm ASTM International, PA, USA), wherein samples were incubated in physiological DPBS at physiological temperature for time points of 3, 6, 12, and 16 weeks. Dimensions, weight and density of samples were recorded.

Results

Table 1a shows the static pull-out performance results of swivel and non-swivel suture anchors (n=6 for each group at each time point, with n=10 for time zero) and Table 1b shows the dynamic pull-out performance results for these anchors (individual results).

TABLE 1a

Peak pull-out force results for non-swivel suture anchors as compared with swivel suture anchors

| Weeks of Degradation | Pull out force (N) for Fiber-Reinforced Non-Swivel Anchor | Pull out force (N) for Commercial Swivel Anchor |
|---|---|---|
| 0 | 289.78 ± 13.31 | 219.94 ± 34.42 |
| 3 | 270.57 ± 25.22 | 205.73 ± 8.61 |

TABLE 1a-continued

Peak pull-out force results for non-swivel suture anchors as compared with swivel suture anchors

| Weeks of Degradation | Pull out force (N) for Fiber-Reinforced Non-Swivel Anchor | Pull out force (N) for Commercial Swivel Anchor |
|---|---|---|
| 6 | 253.42 ± 16.48 | 195.33 ± 13.71 |
| 12 | 270.75 ± 8.78 | 191.31 ± 21.59 |
| 16 | 252.28 ± 12.47 | 185.33 ± 17.68 |

TABLE 1b

Cycles of force loading until runout for non-swivel suture anchors as compared with swivel suture anchors

| Weeks of Degradation | Number of cycles until runout for Fiber-Reinforced Non-Swivel Anchor (two samples tested) | Number of cycles until runout for Commercial Swivel Anchor (three samples tested) |
|---|---|---|
| 0 | 100,000 | 5,895 |
| | 130,378 | 15,135 |
| | | 12,514 |
| 3 | 53,446 | 2,261 |
| | 46,411 | 10 |
| | | 308 |
| 6 | 28,069 | 659 |
| | 56,162 | 2,554 |
| | | 5,096 |
| 12 | 33,317 | 2,205 |
| | 51,538 | 178 |
| | | 489 |
| 16 | 97,753 | 63 |
| | 39,315 | 733 |
| | | 1 |

The above results indicate that both in static and dynamic testing, a non-swivel suture anchor that is configured as described herein results in substantially stronger anchoring than the commercially-available swivel suture anchor.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for securing a suture to a bone, the apparatus comprising:
- a non-swivel suture anchor, comprising:
  - a tip component configured to be advanced into a hole within the bone, the tip component comprising:
  - a distal portion having a distal end configured to be advanced into the bone;
  - a proximal portion extending proximally from the distal portion;
    - a widened end portion at a distal region of the distal portion, the widened end portion defining an eyelet that is configured to receive the suture, wherein the eyelet extends through the widened end portion transversely;
    - a shaft that projects axially from the widened end portion toward the proximal portion, the shaft defining a widened shaft portion proximate to the widened end portion, the widened shaft portion being wider than a remainder of the shaft and being narrower than the widened end portion;
    - wherein the widened shaft portion is configured to center the tip component and prevent the tip component from swiveling once a cannulated screw is advanced over the widened shaft portion; and
  - a cannulated screw configured to secure the tip component within the hole within the bone, the cannulated screw defining a lumen therethrough that is sized such that as the cannulated screw is advanced over the widened shaft portion, an inner surface of the cannulated screw engages the widened shaft portion;
  - wherein the widened shaft portion is sized such that when the cannulated screw is advanced over the widened shaft portion, the widened shaft portion tightly fits within the inner surface of the cannulated screw such that the tip component is unable to swivel with respect to the cannulated screw;
- wherein:
  - the tip component further comprises a plurality of ramped tip teeth disposed circumferentially around the shaft;
  - the cannulated screw further comprises a plurality of ramped screw teeth that are arranged circumferentially within the lumen, and
  - the tip teeth and the screw teeth are configured to engage each other, such that when they are engaged the cannulated screw is not swivelable with respect to the tip component.

2. The apparatus according to claim 1, wherein the widened shaft portion is configured to center the tip component with respect to the cannulated screw, thereby maintaining axial orientation of the tip component within the bone in the presence of asymmetrical pull-out forces exerted by the suture, and wherein the engagement of the inner surface of the cannulated screw with the widened shaft portion is such that the tip component is unable to swivel with respect to the cannulated screw.

3. The apparatus according to claim 1, wherein a difference between a diameter of the widened shaft portion and a diameter defined by the inner surface of the cannulated screw is less than 0.5 mm, 0.4 mm, 0.2 mm or 0.1 mm.

4. The apparatus according to claim 1, wherein the inner surface of the cannulated screw has a polygonal shape, and wherein a difference between a diameter of the widened shaft portion and a distance between opposing edges of the polygon defined by inner surface of the cannulated screw is less than 0.5 mm, 0.4 mm, 0.2 mm, or 0.1 mm.

5. The apparatus according to claim 1, wherein the tip component comprises a fiber-reinforced biocomposite material comprising a polymer and one or more reinforcing fibers.

6. The apparatus according to claim 5, wherein the cannulated screw comprises a fiber-reinforced biocomposite material comprising a polymer and one or more reinforcing fibers.

7. The apparatus according to claim 5, wherein at least some of the reinforcing fibers at least partially encircle the eyelet.

8. The apparatus according to claim 7, wherein between 8,000 and 20,000 of the reinforcing fibers at least partially encircle the eyelet.

9. The apparatus according to claim 1, wherein
- the widened shaft portion comprises a frusto-conical taper transitioning from a narrower proximal region to a wider distal region, the taper being configured such that as the cannulated screw is advanced distally over the widened shaft portion, the inner surface of the cannulated screw progressively engages the widened shaft portion.

10. Apparatus for securing a suture to a bone, the apparatus comprising:

a non-swivel suture anchor, comprising:

a tip component configured to be axially advanced over the shaft of the tip component advanced into a hole within the bone, the tip component comprising:

a widened end portion that defines an eyelet that is configured to receive the suture;

a shaft that projects axially from the widened end portion;

and one or more tip teeth disposed circumferentially around the shaft, the tip teeth extending axially along the shaft and being arranged at a common axial position around a circumference of the shaft; and a cannulated screw configured to secure the tip component within the hole within the bone, the cannulated screw defining a lumen therethrough and defining one or more screw teeth that are arranged circumferentially within the lumen at a common axial position, the tip teeth and the screw teeth being configured to engage each other upon axial advancement of the cannulated screw over the shaft, such that when they are engaged the tip component is not swivelable with respect to the cannulated screw;

wherein:

wherein the tip teeth and screw teeth have ramped surfaces that are configured to engage each other, where said ramped engagement surfaces are configured to engage corresponding ramped surfaces of the screw teeth as the cannulated screw is advanced axially.

11. The apparatus according to claim 10, wherein the tip component comprises between 2 and 10 teeth and the cannulated screw comprises between 2 and 10 teeth.

12. The apparatus according to claim 11, wherein the tip component comprises between 2 and 6 teeth and the cannulated screw comprises between 2 and 6 teeth.

13. The apparatus according to claim 10, wherein:

the shaft of the tip component defines a widened shaft portion proximate to the widened end portion, the widened shaft portion being narrower than the widened end portion and being wider than a remainder of the shaft, and the lumen of the cannulated screw is sized such that as the cannulated screw is advanced over the widened shaft portion, an inner surface of the cannulated screw engages the widened shaft portion.

14. The apparatus according to claim 13, wherein the tip teeth are disposed circumferentially around the widened shaft portion.

15. A method comprising:

securing a suture to a bone, using the non-swivel suture anchor of claim 1, by:

creating a hole in the bone;

inserting the suture into an eyelet of a tip component of the non-swivel suture anchor;

advancing the tip component into the hole, the tip component including:

a widened end portion that defines the eyelet, and a shaft that projects axially from the widened end portion, the shaft defining a widened shaft portion proximate to the widened end portion, the widened shaft portion being wider a remainder of the shaft and being narrower than the widened end portion; and securing the tip component within the hole by advancing a cannulated screw over the shaft of the tip component, the cannulated screw defining a lumen therethrough that is sized such that as the cannulated screw is advanced over the widened shaft portion, the inner surface of the cannulated screw engages the widened shaft portion.

* * * * *